United States Patent
Robinson et al.

(10) Patent No.: US 9,737,660 B2
(45) Date of Patent: Aug. 22, 2017

(54) DRUG INFUSION DEVICE WITH CONTROLLABLE VALVE

(75) Inventors: Reginald D. Robinson, Plymouth, MN (US); Mary E. Robischon, Minneapolis, MN (US); Bernard Q. Li, Plymouth, MN (US); Irfan Z. Ali, Woodbury, MN (US); Steven R. Christenson, Coon Rapids, MN (US); Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/217,981

(22) Filed: Aug. 25, 2011

(65) Prior Publication Data

US 2012/0053514 A1 Mar. 1, 2012

Related U.S. Application Data

(60) Provisional application No. 61/376,835, filed on Aug. 25, 2010.

(51) Int. Cl.
| | |
|---|---|
| *A61M 5/168* | (2006.01) |
| *A61M 39/22* | (2006.01) |
| *A61M 5/142* | (2006.01) |

(52) U.S. Cl.
CPC .... *A61M 5/16827* (2013.01); *A61M 5/14276* (2013.01); *A61M 5/1684* (2013.01); *A61M 39/223* (2013.01); *A61M 2205/3523* (2013.01); *A61M 2205/3569* (2013.01); *A61M 2210/1003* (2013.01)

(58) Field of Classification Search
CPC .......... A61M 5/16813; A61M 5/14276; A61M 5/16827; A61M 5/16804; A61M 39/223

USPC .... 604/31, 65, 67, 167.01, 167.05, 246-248
See application file for complete search history.

(56) References Cited

U.S. PATENT DOCUMENTS

| | | | |
|---|---|---|---|
| 2,911,123 | A | 11/1959 | Saccomanno |
| 3,923,060 | A | 12/1975 | Ellinwood, Jr. |
| (Continued) | | | |

FOREIGN PATENT DOCUMENTS

| | | |
|---|---|---|
| WO | 9312825 A1 | 7/1993 |
| WO | 2005007223 A2 | 1/2005 |
| WO | 2010096449 A2 | 8/2010 |

OTHER PUBLICATIONS

U.S. Appl. No. 13/220,359, filed Aug. 29, 2011, Petri.
(Continued)

*Primary Examiner* — Imani Hayman
*Assistant Examiner* — Jenna Zhang
(74) *Attorney, Agent, or Firm* — Shumaker & Sieffert, P.A.

(57) ABSTRACT

A therapeutic fluid delivery device that includes at least one controllable valve is generally described. In one example, an implantable therapeutic fluid delivery system includes a first fluid pathway configured to convey a first therapeutic fluid and a second fluid pathway configured to convey a second therapeutic fluid, the second fluid pathway being separate from the first fluid pathway. The therapeutic fluid delivery system includes a valve connected to the first fluid pathway and the second fluid pathway, and a processor configured to control actuation of the valve to open and close the first fluid pathway and to open and close the second fluid pathway.

45 Claims, 10 Drawing Sheets

(56) References Cited

U.S. PATENT DOCUMENTS

| | | | |
|---|---|---|---|
| 4,193,397 A * | 3/1980 | Tucker | A61M 5/14276 604/131 |
| 4,496,343 A | 1/1985 | Prosl et al. | |
| 4,571,749 A | 2/1986 | Fischell | |
| 4,573,994 A | 3/1986 | Fischell et al. | |
| 4,604,090 A | 8/1986 | Reinicke | |
| 4,710,174 A | 12/1987 | Moden et al. | |
| 4,714,462 A | 12/1987 | DiDomenico | |
| 4,832,054 A | 5/1989 | Bark | |
| 4,955,861 A | 9/1990 | Enegren et al. | |
| 4,978,338 A | 12/1990 | Melsky et al. | |
| 5,006,115 A | 4/1991 | McDonald | |
| 5,226,879 A | 7/1993 | Ensminger et al. | |
| 5,263,930 A | 11/1993 | Ensminger | |
| 5,328,465 A | 7/1994 | Kratoska et al. | |
| 5,336,194 A | 8/1994 | Polaschegg et al. | |
| 5,395,324 A | 3/1995 | Hinrichs et al. | |
| 5,667,504 A | 9/1997 | Baumann et al. | |
| 5,695,490 A | 12/1997 | Flaherty et al. | |
| 5,769,823 A | 6/1998 | Otto | |
| 5,814,019 A | 9/1998 | Steinbach et al. | |
| 5,820,589 A | 10/1998 | Torgerson et al. | |
| 6,190,352 B1 | 2/2001 | Haarala et al. | |
| 6,293,922 B1 | 9/2001 | Haase | |
| 6,416,495 B1 * | 7/2002 | Kriesel | A61M 5/152 604/132 |
| 6,459,917 B1 | 10/2002 | Gowda et al. | |
| 6,471,675 B1 * | 10/2002 | Rogers | A61M 5/14276 604/151 |
| 6,554,822 B1 | 4/2003 | Holschneider et al. | |
| 6,764,472 B1 | 7/2004 | Burke et al. | |
| 7,811,279 B2 | 10/2010 | John | |
| 7,914,499 B2 | 3/2011 | Gonnelli et al. | |
| 8,348,909 B2 | 1/2013 | Haase et al. | |
| 8,721,605 B2 | 5/2014 | Brandt et al. | |
| 2001/0020471 A1 | 9/2001 | Kitten | |
| 2002/0156462 A1 | 10/2002 | Stultz | |
| 2003/0050623 A1 | 3/2003 | Lord et al. | |
| 2003/0133358 A1 | 7/2003 | Karp | |
| 2003/0176833 A1 * | 9/2003 | Libermann | A61M 3/0241 604/65 |
| 2004/0073196 A1 | 4/2004 | Adams | |
| 2004/0143242 A1 | 7/2004 | Ludin et al. | |
| 2005/0070875 A1 | 3/2005 | Kulessa | |
| 2005/0113745 A1 | 5/2005 | Stultz | |
| 2005/0256451 A1 | 11/2005 | Adams et al. | |
| 2005/0273083 A1 | 12/2005 | Lebel et al. | |
| 2006/0089619 A1 | 4/2006 | Ginggen | |
| 2006/0142705 A1 * | 6/2006 | Halili | A61M 5/14276 604/288.01 |
| 2006/0270983 A1 | 11/2006 | Lord et al. | |
| 2006/0271021 A1 | 11/2006 | Steinbach | |
| 2006/0271022 A1 | 11/2006 | Steinbach et al. | |
| 2007/0197968 A1 * | 8/2007 | Pongpairochana | A61M 5/20 604/131 |
| 2007/0255235 A1 | 11/2007 | Olsen et al. | |
| 2007/0255237 A1 | 11/2007 | Lobl et al. | |
| 2007/0255261 A1 | 11/2007 | Haase | |
| 2008/0039820 A1 | 2/2008 | Sommers et al. | |
| 2008/0060442 A1 | 3/2008 | Smith | |
| 2008/0243093 A1 * | 10/2008 | Kalpin | A61B 17/3403 604/288.02 |
| 2008/0287887 A1 * | 11/2008 | Mack | A61M 5/1413 604/247 |
| 2009/0227989 A1 | 9/2009 | Burke et al. | |
| 2010/0089487 A1 | 4/2010 | Burke et al. | |
| 2010/0125246 A1 | 5/2010 | Kalpin | |
| 2010/0274196 A1 * | 10/2010 | Brandt | A61M 5/14276 604/175 |
| 2011/0166522 A1 | 7/2011 | Haase et al. | |
| 2011/0172633 A1 | 7/2011 | Ali et al. | |

OTHER PUBLICATIONS

U.S. Appl. No. 13/218,007, filed Aug. 25, 2011, Haase.
Response to Office Action dated Aug. 12, 2014, from U.S. Appl. No. 13/218,007, filed Nov. 12, 2014, 18 pp.
Office Action from U.S. Appl. No. 13/218,007, dated Aug. 12, 2014, 16 pp.
Response to Office Action dated Oct. 2, 2014, from U.S. Appl. No. 13/220,359, dated Dec. 23, 2014, 16 pp.
Office Action from U.S. Appl. No. 13/220,359, dated Oct. 2, 2014, 11 pp.
Final Office Action from U.S. Appl. No. 13/220,359, dated Feb. 26, 2015, 17 pp.
Final Office Action from U.S. Appl. No. 13/218,007, dated Feb. 3, 2015, 26 pp.
Office Action from U.S. Appl. No. 13/218,007, dated Aug. 13, 2015, 18 pp.
Response to Office Action dated Aug. 13, 2015, from U.S. Appl. No. 13/218,007, filed Nov. 13, 2015, 16 pp.
Final Office Action from U.S. Appl. No. 13/218,007, dated Jan. 21, 2016, 23 pp.
Response to the Office Action mailed Jun. 27, 2016, from U.S. Appl. No. 13/218,007, filed Sep. 27, 2016, 15 pp.
Office Action from U.S. Appl. No. 13/218,007 dated Jun. 27, 2016, 17 pp.
Response to Office Action mailed Jan. 21, 2016, from U.S. Appl. No. 13/218,007, filed Apr. 21, 2016, 14 pp.
Response to Office Action mailed Dec. 2, 2016, from U.S. Appl. No. 13/218,007, filed Feb. 2, 2017, 7 pp.
Advisory Action from U.S. Appl. No. 13/218,007, dated Feb. 14, 2017, 3 pp.
Final Office Action from U.S. Appl. No. 13/218,007 dated Dec. 2, 2016, 20 pp.
Appeal Brief for U.S. Appl. No. 13/218,007, filed May 8, 2017, 30 pp.
Pre-Appeal Brief Request for Review for U.S. Appl. No. 13/218,007, filed Mar. 2, 2017, 5 pp.
Examiner's Answer from U.S. Appl. No. 13/218,007, dated Jun. 14, 2017, 25 pp.

* cited by examiner

DRUG INFUSION DEVICE WITH CONTROLLABLE VALVE

This application claims the benefit of U.S. Provisional Application No. 61/376,835, filed Aug. 25, 2010, the entire content of which is incorporated herein by this reference.

TECHNICAL FIELD

This disclosure generally relates to implantable medical devices and, more particularly, to implantable fluid delivery devices.

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic fluids, such as drugs to patients. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device that can deliver a drug or other therapeutic fluid to a patient at a selected site. A drug infusion device may be partially or completely implanted at a location in the body of a patient and deliver a fluid medication through a catheter to a selected delivery site in the body. Drug infusion devices, such as implantable drug pumps, commonly include a reservoir for holding a supply of the therapeutic fluid, such as a drug, for delivery to a site in the patient. The fluid reservoir can be self-sealing and accessible through one or more ports. A pump is fluidly coupled to the reservoir for delivering the therapeutic fluid to the patient. A catheter provides a pathway for delivering the therapeutic fluid from the pump to a delivery site in the patient.

SUMMARY

In general, the disclosure describes fluid delivery devices that include at least one controllable valve. In some examples, a controllable valve is in fluid communication with an inlet port of a fluid delivery device. In other examples, a controllable valve is in fluid communication with a sensor of a fluid delivery device that is configured to measure a fluid characteristic. Other valve configurations are also presented. In any configuration, actuation of the valve may open and close different fluid pathways. As a result, controlled access to different fluid pathways may be provided by using a controllable valve.

In one example, an implantable therapeutic fluid delivery system includes a first fluid pathway configured to convey a first therapeutic fluid and a second fluid pathway configured to convey a second therapeutic fluid, the second fluid pathway being separate from the first fluid pathway. The system also includes a valve connected to the first fluid pathway and the second fluid pathway and a processor configured to actuate the valve to open and close the first fluid pathway and to open and close the second fluid pathway.

In another example, a method includes actuating a valve within an implantable fluid delivery device to open and close at least one of a first fluid pathway and a second fluid pathway. According to the example, the first fluid pathway is configured to convey a first therapeutic fluid, the second fluid pathway is configured to convey a second therapeutic fluid, the second fluid pathway is separate from the first fluid pathway, and the valve is connected to the first fluid pathway and the second fluid pathway.

In another example according to this disclosure, a computer-readable storage medium is provided that includes instructions that cause a programmable processor to control actuation of a valve within an implantable fluid delivery device to open and close at least one of a first fluid pathway and a second fluid pathway. The example further provides that the first fluid pathway is configured to convey a first therapeutic fluid, the second fluid pathway is configured to convey a second therapeutic fluid, the second fluid pathway is separate from the first fluid pathway, and the valve is connected to the first fluid pathway and the second fluid pathway.

In another example, a fluid delivery system includes a valve within an implantable fluid delivery device connected to a first fluid pathway and a second fluid pathway and means for actuating the valve to open and close at least one of the first fluid pathway and the second fluid pathway. In the system, the first fluid pathway is configured to convey a first therapeutic fluid, the second fluid pathway is configured to convey a second therapeutic fluid, and the second fluid pathway is separate from the first fluid pathway.

In another example, a method includes receiving user input specifying an implantable fluid delivery device to be refilled, displaying an indication of the fluid delivery device to be refilled based on the received user input, receiving user input assigning a therapeutic fluid to be housed in a reservoir of the implantable fluid delivery device to the reservoir of the implantable fluid delivery device, and in response to the received user input assigning the therapeutic fluid, issuing instructions to control actuation of a valve to open a fluid pathway configured to provide fluid communication between an inlet port of the implantable fluid delivery device and the reservoir.

In another example, a therapeutic fluid delivery system includes an implantable fluid delivery device comprising a reservoir configured to house a therapeutic fluid, an inlet port configured to receive a fluid delivery system, and a valve connected to a fluid pathway configured to provide fluid communication between the inlet port and the reservoir. The system also includes a programmer comprising a processor, where the processor is configured to cause to the programmer to receive user input specifying that the fluid delivery device is to be refilled, display an indication of the fluid delivery device based on the received user input, receive user input assigning the therapeutic fluid to be housed in the reservoir of the fluid delivery device to the reservoir of the fluid delivery device, and in response to the received user input assigning the therapeutic fluid, and issue instructions to control actuation of the valve to open the fluid pathway.

In another example, a computer-readable storage medium is presented that includes instructions that cause a programmable processor to receive a user input specifying that an implantable fluid delivery device is to be refilled, display an indication of the fluid delivery device based on the received user input, receive a user input assigning a therapeutic fluid to be housed in a reservoir of the implantable fluid delivery device to the reservoir of the fluid delivery device, in response to the received user input assigning the therapeutic fluid, issue instructions to control actuation of the valve to open the fluid pathway.

In another example, a therapeutic fluid delivery system includes a first implantable fluid delivery device comprising a first reservoir configured to house a first therapeutic fluid, and a second implantable fluid delivery device comprising a second reservoir configured to house a second therapeutic fluid. The therapeutic fluid delivery system also includes a programmer comprising a processor, where the processor is configured to cause to the programmer to at least receive user input specifying that at least one of the first implantable fluid delivery device or the second implantable fluid delivery device is to be refilled, display an indication of the at least one of the first implantable fluid delivery device or the second implantable fluid delivery device based on the received user input, receive user input assigning at least one of the first therapeutic fluid or the second therapeutic fluid to at least one of the first reservoir of the first implantable fluid delivery device or the second reservoir of the second implantable fluid delivery device, in response to the received user input assigning at least one of the first therapeutic fluid or the second therapeutic fluid, and provide a command prompt guiding the user to refill at least one of the first implantable fluid delivery device or the second implantable fluid delivery device.

The details of one or more examples disclosed herein are set forth in the accompanying drawings and the description below. Other features, objects, and advantages will be apparent from the description and drawings, and from the claims.

DETAILED DESCRIPTION

Figure 1:
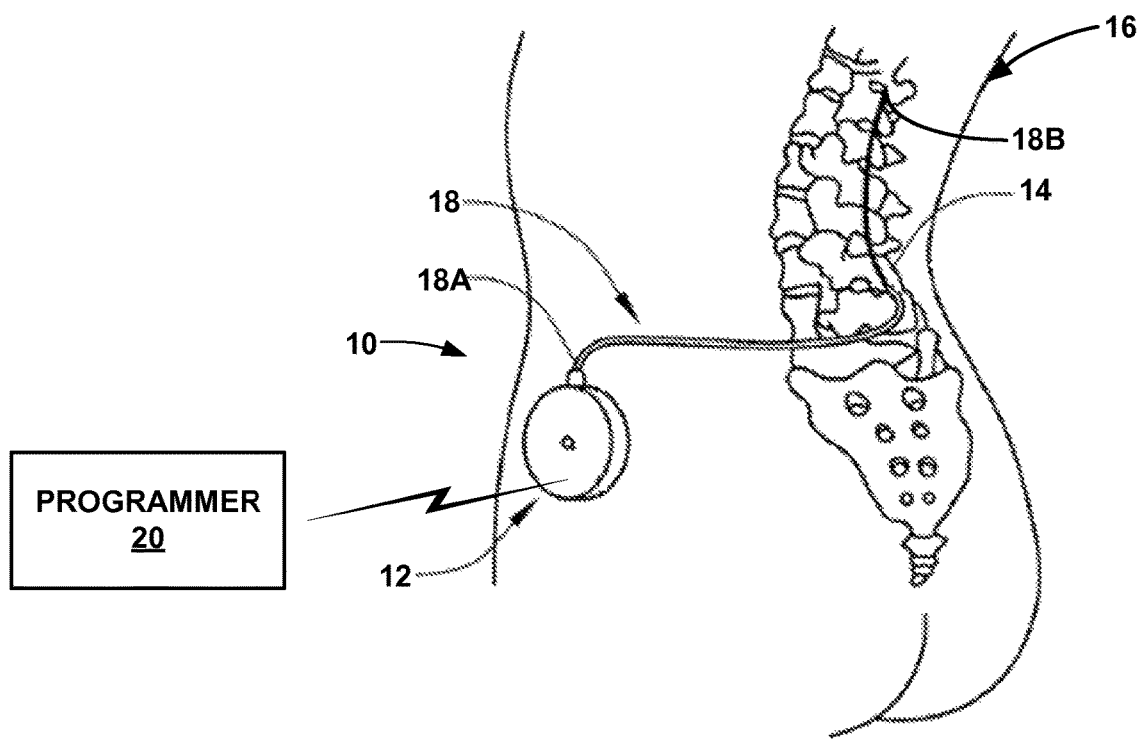
FIG. 1 is a conceptual diagram illustrating an example of a fluid delivery system including an implantable fluid delivery device configured to deliver a therapeutic fluid to a patient via a catheter.

An implantable fluid delivery device may be implanted in the body of a patient to deliver a fluid, such as a drug or other therapeutic agent, through a catheter to one or more selected delivery sites within the body of the patient. The implantable fluid delivery device may include a reservoir for storing the therapeutic agent prior to delivery to the patient. The implantable fluid delivery device may also include an inlet port, such as a refill port, to facilitate in-service refilling of the fluid reservoir over the service life of the implantable fluid delivery device. The inlet port may be connected to the reservoir by a fluid pathway. A needle or syringe may be percutaneously inserted into the inlet port to add therapeutic agent to the fluid reservoir through the fluid pathway. Alternatively, the inlet port can be used to remove therapeutic agent from fluid reservoir. For example, a therapeutic agent may be removed from the fluid reservoir prior to refilling the fluid reservoir with a different type of therapeutic agent.

An implantable fluid delivery device may also include a fluid pathway that is in direct fluid communication with a catheter that is located in the body of the patient. That is, the implantable fluid delivery device may include a fluid pathway that does not pass through a reservoir or a pump that may be associated with the implantable fluid delivery device but instead provides direct fluid access to the catheter. The direct catheter fluid pathway may also be accessed through an inlet port, such as a catheter inlet port (which may also be referred to as a catheter access port) that is separated from the fluid reservoir refill inlet port. However, the catheter inlet port may serve a different function than the fluid refill inlet port. For example, the catheter inlet port may be used to provide a direct injection to the patient, such as direct injection of a therapeutic agent or a direct injection of a dye for dye study testing. The catheter inlet port may also be used to remove fluid from the body of a patient for testing or analysis. For example, cerebrospinal fluid may be removed from a patient with a catheter implanted in an epidural space.

In addition to, or instead of, a catheter inlet port and a fluid refill inlet port, an implantable fluid delivery device may include different fluid pathways that are accessible through one or more different inlet ports. For example, the implantable fluid delivery device may include multiple fluid reservoirs, such as two reservoirs, to store different therapeutic agents or different quantities of the same therapeutic agent. Each fluid reservoir may be accessed through separate inlet ports. In this manner, each fluid reservoir may be accessed by a dedicated inlet port that is connected to a dedicated fluid pathway.

It is generally useful for the safe and intended operation of the fluid delivery device if a user, such as a patient or clinician, can readily distinguish between different inlet ports that are connected to different fluid pathways. In some examples, a user may rely on the physical geometry of the fluid delivery device and tactile feel to distinguish between different inlet ports on the fluid delivery device. In other examples, a user may also employ an external aid, such as a template, to identify and distinguish between different inlet ports on the fluid delivery device.

In accordance with the techniques described in this disclosure, a fluid delivery device with at least one inlet port connected to different fluid pathways is provided. The fluid delivery device may include at least one valve that can close some or all fluid pathways. The at least one valve may also provide controlled access to at least one fluid pathway. A fluid delivery device with fewer inlet ports may be more user friendly than a comparable fluid delivery device with more inlet ports. In addition, a fluid delivery device valve may provide an additional mechanical barrier that can prevent inadvertent fluid discharges, thus increasing the overall integrity of the fluid delivery device.

In some examples according to this disclosure, an external controller, such as a programmer, is provided with a fluid delivery device to control the at least one valve. A user can operate the programmer to selectively open and close different fluid pathways, thus providing selectable access to different fluid pathways through a single inlet port. However, in some examples, the at least one valve may not provide access to any fluid pathways unless appropriate authorization is provided. In other words, the fluid delivery device may be "locked out" unless a user can provide authentication. A locked out fluid delivery device can prevent unauthorized refills of a device (e.g., an attempted patient refill where clinician refill is required). A locked out fluid delivery device can also prevent misappropriation and misuse of therapeutic agents (e.g., morphine) housed in a reservoir by unauthorized withdrawal of fluids.

In view of the advantages of having a fluid delivery device with at least one controllable valve at an inlet port, this disclosure describes other fluid delivery devices that have at least one controllable valve between different fluid pathways in addition to, or instead of, at an inlet port. For example, a fluid delivery device may include at least one controllable valve interposed between different fluid pathways and a sensor. The at least one controllable valve can be actuated to separately measure a fluid characteristic in each of the different fluid pathways, thus reducing the number of sensors in the device and mitigating inconsistencies that may be present between different sensors of the device. As another example, a fluid delivery device may include at least one controllable valve to control fluid pathways to or from multiple pumping mechanisms disposed within the fluid delivery device. As another example, a fluid delivery device may include at least one controllable valve interposed between a pumping mechanism disposed within the fluid delivery device and a multisite injection discharge port, such as a catheter connection port configured to connect to a catheter with multiple lumens or a catheter connection port configured to connect to multiple catheters. Thus, the at least one controllable valve can control the delivery of different therapeutic agents and/or the delivery rate of a therapeutic agent to multiple target therapy locations. Example fluid therapy delivery devices and valves will be described in greater detail with reference to FIGS. 4-9. However, an example fluid delivery system including an implantable fluid delivery device and external programmer will first be described with reference to FIGS. 1-3.

FIG. 1 is a conceptual diagram illustrating an example of a therapy system 10, which includes implantable medical device (IMD) 12, catheter 18, and external programmer 20. IMD 12 is connected to at least one catheter 18 to deliver at least one therapeutic fluid, e.g. a pharmaceutical agent, pain relieving agent, anti-inflammatory agent, gene therapy agent, or the like, to a target site within patient 16. IMD 12 includes an outer housing that, in some examples, is constructed of a biocompatible material that resists corrosion and degradation from bodily fluids including, e.g., titanium or biologically inert polymers. IMD 12 may be implanted within a subcutaneous pocket relatively close to the therapy delivery site. For example, as shown in FIG. 1, IMD 12 may be implanted within an abdomen of patient 16. In other examples, IMD 12 may be implanted within other suitable sites within patient 16, which may depend, for example, on the target site within patient 16 for the delivery of the therapeutic fluid. In still other examples, device 12 may be external to patient 16 with a percutaneous catheter connected between device 12 and the target delivery site within patient 16. In these examples, device 12 is not an implantable medical device but rather an external medical device.

As described in greater detail below, IMD 12 includes at least one valve connected to at least two different fluid pathways in IMD 12. In one example, IMD 12 includes at least one valve to open and close a first fluid pathway between an inlet port and catheter 18 and to open and close a second fluid pathway between the inlet port and a therapeutic fluid reservoir. For example, in some cases, IMD 12 includes a first valve to open and close a first fluid pathway between an inlet port and catheter 18 and a second valve to open and close a second fluid pathway between the inlet port and a therapeutic fluid reservoir. In another example, IMD 12 includes at least two therapeutic fluid reservoirs and at least one valve to open and close a first fluid pathway between an inlet port and the first therapeutic fluid reservoir and to open and close a second fluid pathway between the inlet port and a second therapeutic fluid reservoir.

IMD 12 delivers a therapeutic fluid from a reservoir (not shown) to patient 16 through catheter 18 from proximal end 18A coupled to IMD 12 to distal end 18B located proximate to the target site. Example therapeutic fluids that may be delivered by IMD 12 include, e.g., insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy drugs or agents, anticoagulants, cardiovascular medications or chemotherapeutics.

Catheter 18 can comprise a unitary catheter or a plurality of catheter segments connected together to form an overall catheter length. In addition, catheter 18 may be a single-lumen catheter or a multi-lumen catheter. Catheter 18 may be coupled to IMD 12 either directly or with the aid of a catheter extension (not shown in FIG. 1). In the example shown in FIG. 1, catheter 18 traverses from the implant site of IMD 12 to one or more targets proximate to spinal cord 14, e.g., within an intrathecal space or epidural space. Catheter 18 is positioned such that one or more fluid delivery outlets (not shown in FIG. 1) of catheter 18 are proximate to the targets within patient 16. In the example of FIG. 1, IMD 12 delivers a therapeutic fluid through catheter 18 to one or more targets proximate to spinal cord 14.

IMD 12 can be configured for intrathecal drug delivery into the intrathecal space, as well as epidural delivery into the epidural space, both of which surround spinal cord 14. In some examples, multiple catheters may be coupled to IMD 12 to target the same or different nerve sites or other tissue sites within patient 16, or catheter 18 may include multiple lumens to deliver multiple therapeutic fluids to the patient. Therefore, although the target site shown in FIG. 1 is proximate to spinal cord 14 of patient 16, other applications of therapy system 10 may include alternative target delivery sites in addition to or in lieu of the spinal cord of the patient. For example, therapy system 10 may be configured to deliver single or multisite deep-brain infusion therapy.

Programmer 20 is an external computing device that is configured to communicate with IMD 12 by wireless telemetry as needed, such as to provide or retrieve therapy information or control aspects of therapy delivery (e.g., modify the therapy parameters such as rate or timing of delivery, turn IMD 12 on or off, and so forth) from IMD 12 to patient 16. In some examples, programmer 20 may be a clinician programmer that the clinician uses to communicate with IMD 12, program therapy delivered by IMD 12, and actuate a controllable valve in IMD 12. Alternatively, programmer 20 may be a patient programmer that allows patient 16 to view and modify therapy parameters associated with therapy programs or actuate a controllable valve in IMD 12. The clinician programmer may include additional or alternative programming features than the patient programmer. For example, more complex or sensitive tasks may only be allowed by the clinician programmer to prevent patient 16 from making undesired or unsafe changes to the operation of IMD 12. Programmer 20 may be a handheld or other dedicated computing device, or a larger workstation or a separate application within another multi-function device.

As described in greater detail below, IMD 12, alone or in cooperation with programmer 20 or another external device communicatively connected to IMD 12, is configured to selectively control at least one valve connected to at least two different fluid pathways in IMD 12. In one example, IMD 12 controls at least one valve located proximate an inlet port of IMD 12. By controlling the at least one valve proximate the inlet port, IMD 12 provides access to multiple fluid pathways through a single inlet port. In another example, IMD 12 controls at least one valve interposed between at least one fluid pathway and a sensor. The sensor can detect a fluid characteristic when the at least one valve is opened to expose the sensor to the fluid in the at least one fluid pathway.

Additionally, IMD 12, alone or in cooperation with programmer 20 or another external device communicatively connected to IMD 12, is configured to control entry and removal of fluids from IMD 12. In one example, different fluid pathways of IMD 12 may be opened and closed via programmer 20. A textual or graphical representation of at least one fluid pathway that is open or closed in IMD 12 may be displayed via programmer 20. In another example, a fluid reservoir of IMD 12 may be a display of programmer 20, which may display a textual or graphical representation of the volume of fluid in the reservoir during a refill operation. In another example, the fluid reservoir of IMD 12 may be a separate display or display of another device, e.g. a laptop, desktop, or server computer, which is communicatively connected to IMD 12 and configured to display a text or graphical representation of the volume of fluid in the reservoir.

Figure 2:
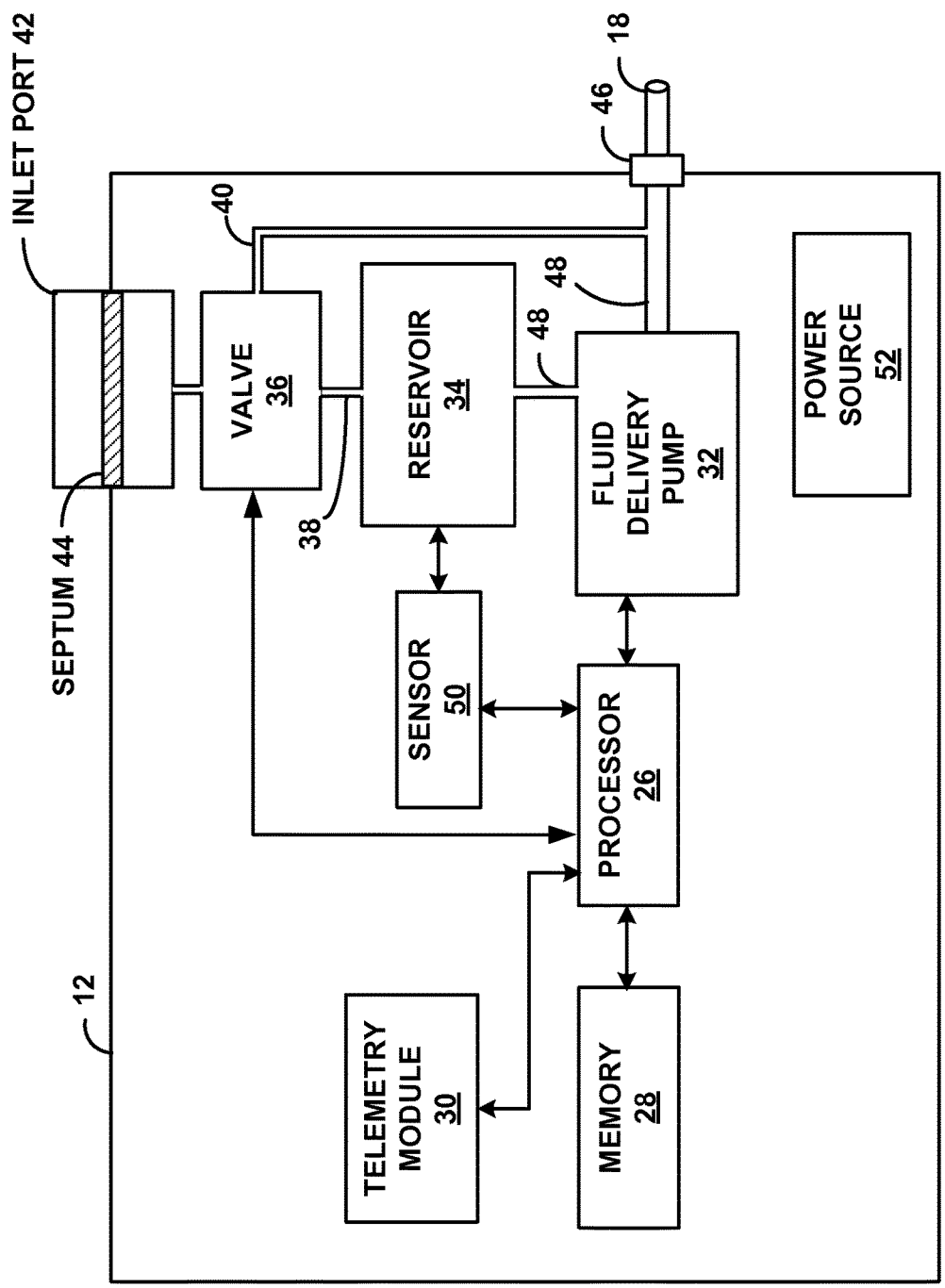
FIG. 2 is a functional block diagram illustrating an example of the implantable fluid delivery device of FIG. 1.

FIG. 2 is a functional block diagram illustrating components of an example of IMD 12, which includes processor 26, memory 28, telemetry module 30, fluid delivery pump 32, reservoir 34, valve 36, reservoir fluid pathway 38, catheter access fluid pathway 40, inlet port 42, septum 44, catheter connection port 46, internal fluid pathways 48, sensor 50 and power source 52. Processor 26 is communicatively connected to memory 28, telemetry module 30, fluid delivery pump 32, valve 36, and sensor 50. Fluid delivery pump 32 is connected to reservoir 34 and internal fluid pathways 48. Reservoir 34 is connected to inlet port 42 through valve 36 and reservoir fluid pathway 38, which extends from valve 36 to reservoir 34. Inlet port 42 includes septum 44. Catheter connection port 46 is connected to catheter 18. Inlet port 42 is directly connected to catheter connection port 46 through valve 36 and catheter access fluid pathway 40, which extends from valve 36 to catheter connection port 46.

IMD 12 also includes power source 44, which is configured to deliver operating power to various components of the IMD. As described in greater detail with respect to FIG. 4, IMD 12 may include a plurality of reservoirs for storing more than one type of therapeutic fluid or for storing different amounts of therapeutic fluid. In some examples, IMD 12 may include a single long tube that contains therapeutic fluid in place of a reservoir. However, for ease of description, IMD 12 in FIG. 2 includes a single reservoir 34.

During operation of IMD 12, processor 26 controls fluid delivery pump 32 with the aid of instructions associated with program information that is stored in memory 28 to deliver a therapeutic fluid to patient 16 via catheter 18. Instructions executed by processor 26 may, for example, define therapy programs that specify the dose of therapeutic fluid that is delivered to a target tissue site within patient 16 from reservoir 34 via catheter 18. The programs may further specify a schedule of different therapeutic fluid rates and/or other parameters by which IMD 12 delivers therapy to patient 16. The programs may also specify valve actuation commands for controlling valve 36. In some examples, various instructions, such as instructions that define therapy programs, may be stored in a memory of an external device communicatively connected to IMD 12. In one example, therapy program instructions are stored in a memory of programmer 20 and communicated to processor 26 via telemetry module 30.

In general, a therapy program stored on memory 28 and executed by processor 26 defines one or more therapeutic fluid doses to be delivered from reservoir 34 to patient 16 through catheter 18 by IMD 12. A dose of therapeutic fluid generally refers to a total amount of therapeutic fluid, e.g., in volumetric units, delivered over a total amount of time, e.g., twenty-four hour period. The amount of therapeutic fluid in a dose may convey to a caregiver an indication of the probable efficacy of the fluid and the possibility of side effects.

In general, a sufficient amount of the fluid should be administered in order to have a desired therapeutic effect, such as pain relief. However, the amount of the therapeutic fluid delivered to the patient may be limited to a maximum amount, such as a maximum daily amount, in order not to avoid potential side effects. Therapy program parameters specified by a user, e.g., via programmer 20 may include fluid volume per dose, dose time period, maximum dose for a given time interval e.g., daily. In some examples, dosage may also prescribe particular concentrations of active ingredients in the therapeutic fluid delivered by IMD 12 to patient 16.

The manner in which a dose of therapeutic fluid is delivered to patient 16 by IMD 12 may also be defined in the therapy program. For example, processor 26 of IMD 12 may be programmed to deliver a dose of therapeutic fluid according to a schedule that defines different rates at which the fluid is to be delivered at different times during the dose period, e.g. a twenty-four hour period. The therapeutic fluid rate refers to the amount, e.g. in volume, of therapeutic fluid delivered over a unit period of time, which may change over the course of the day as IMD 12 delivers the dose of fluid to patient 16.

As an example, IMD 12 could be programmed to deliver therapeutic fluid to patient 16 at a rate of 20 microliters per hour. In the event the therapy program prescribes this fluid delivery rate for a twenty four hour period and assuming no patient or other boluses during the period of time, the dose of fluid delivered to patient 16 by IMD 12 will be 480 microliters (per twenty four hours). The therapy program may include other parameters, including, e.g., definitions of priming and patient boluses, as well as time intervals between successive patient boluses, sometimes referred to as lock-out intervals.

Therapy programs may be a part of a program group, where the group includes a number of therapy programs. Memory 28 of IMD 12 or a memory associated with programmer 20 may store one or more therapy programs, as well as instructions defining the extent to which patient 16 may adjust therapy parameters, switch between therapy programs, or undertake other therapy adjustments. Patient 16 or a clinician may select and/or generate additional therapy programs for use by IMD 12, e.g., via programmer 20 at any time during therapy or as designated by the clinician.

Components described as processors within IMD 12, external programmer 20, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

In one example, processor 26 of IMD 12 is programmed to deliver a dose of therapeutic fluid to patient 16, which is defined in memory 28 of the device by a volume of therapeutic fluid delivered to the patient in one day. IMD 12 is also programmed according to a therapy schedule such that the fluid is delivered at different rates at different times during the day, which may be stored in the device memory, e.g., as a look-up table associating different fluid rates at different times during the day.

Upon instruction from processor 26, fluid delivery pump 32 draws fluid from reservoir 34 and pumps the fluid through internal fluid pathways 48 to catheter 18 through which the fluid is delivered to patient 16 to effect one or more of the treatments described above in accordance with the program stored on memory 28.

Fluid pathways in IMD 12, such as reservoir fluid pathway 38, catheter access fluid pathway 40, and internal fluid pathways 48, may be segments of tubing or ducts within IMD 12 that allow fluid to be conveyed through IMD 12. In some examples, fluid pathways 48 may be machined or cast into IMD 12. Fluid pathways 38, 40, 48 may be created from a biocompatible material, e.g., titanium, stainless steel, or biologically inert polymer, and sized, e.g., to accommodate desired flow rates in IMD 12.

Fluid delivery pump 32 can be any mechanism that delivers a therapeutic fluid in some metered or other desired flow dosage to the therapy site within patient 16 from reservoir 30 via implanted catheter 18. Fluid delivery pump 32 can be an active pump that allows volumetric flow rates to be manipulated and controlled, e.g., as part of a therapy delivery program or upon receiving instructions from programmer 20. Fluid delivery pump 32 can also be a passive pump that provides a constant volumetric flow rate, with overall fluid delivery controlled by cycling fluid delivery pump 32 on and off. In some examples, IMD 12 may include a plurality of pumps (e.g., two, three, four pumps) that operate at different parameters, e.g., volumetric flow rates, deliver therapeutic fluid to different target sites, or deliver different fluids from different reservoirs within IMD 12. In one example, fluid delivery pump 32 is a squeeze pump that squeezes internal fluid pathway 48 in a controlled manner, e.g., such as a peristaltic pump, to progressively move fluid from reservoir 34 to the distal end of catheter 18 and then into patient 16 according to parameters specified by the therapy program stored on memory 28 and executed by processor 26.

In various examples, fluid delivery pump 32 may be an axial pump, a centrifugal pump, a pusher plate pump, a piston-driven pump, or other means for moving fluid through internal fluid pathways 48 and catheter 18. In one example, fluid delivery pump 32 is an electromechanical pump that delivers fluid by the application of pressure generated by a piston that moves in the presence of a varying magnetic field and that is configured to draw fluid from reservoir 34 and pump the fluid through internal fluid pathways 48 and catheter 18 to patient 16.

In the example of FIG. 1, IMD 12 includes sensor 50 communicatively coupled to processor 26. Sensor 50 may be arranged in a number of locations within IMD 12, including, e.g., in reservoir 34, reservoir fluid pathway 38, catheter access fluid pathway 40, inlet port 42, or internal fluid pathways 48. In some examples, IMD 12 may include multiple sensors, e.g., to measure different fluid characteristics or to measure fluid characteristics in multiple locations. Regardless of where arranged, sensor 50 is configured to measure at least one fluid characteristic in IMD 12. Accordingly, sensor 50 may be any device capable of measuring a fluid characteristic. In various examples, sensor 50 may be a pressure sensor, flow sensor, capacitive sensor, acoustic sensor, optical sensor, pH sensor, temperature sensor or the like. Sensor 50 generates a signal indicative of a fluid characteristic, and the signal is transmitted to processor 26, e.g., for analysis and storage on memory 28.

IMD 12 includes valve 36, which is configured to control fluid communication between inlet port 42, reservoir fluid pathway 38, and catheter access fluid pathway 40. Valve 36 may be arranged in different locations within IMD 12, including, e.g., in or adjacent inlet port 42. Regardless of where arranged, valve 36 is communicatively connected to processor 26. Valve 36 receives instructions from processor 26 to, e.g., actuate in order to open or close at least one of reservoir fluid pathway 38 or catheter access fluid pathway 40, or both reservoir fluid pathway 38 and catheter access fluid pathway 40. Specifically, processor 26 executes instructions and generates control signals, which may be used to control an actuator to open or close valve 36.

Valve 36 may be electronically coupled to processor 26, or a processor of another device, in a variety of ways including electrical wiring (not shown) or a wireless link between valve 36 and the processing device. Valve 36 may be any device that regulates the flow of a fluid by opening, closing, or partially obstructing reservoir fluid pathway 38 and/or catheter access fluid pathway 40. For example, valve 36 may be a three-way valve that regulates flow between inlet port 42 and reservoir fluid pathway 38, and between inlet port 42 and catheter access fluid pathway 40, e.g., on a selective basis such that fluid flow can be directed from inlet port 42 to either reservoir fluid pathway 38 or catheter access fluid pathway. Valve 36 may also correspond to designs described in greater detail with respect to FIGS. 6, 7A-B, and 9. In some examples, valve 36 may includes a plurality of valves for controlling different fluid pathways. For example, valve 36 may include a first valve for controlling fluid communication between inlet port 42 and reservoir fluid pathway 38 and a second valve for controlling fluid communication between inlet port 42 and catheter access fluid pathway 40. In various examples, valve 36 may be a micro-machined valve, such as micro-machined diaphragm valve, ball valve, check valve, gate valve, slide valve, piston valve, rotary valve, or the like. In one example, valve 36 may be a rotary valve in which rotation of valve openings functions to open and closes access to attached fluid pathways 38, 40.

Valve 36 may be arranged in a number of locations within IMD 12, including, e.g., interposed between inlet port 42 and reservoir 34, or interposed between inlet port 42 and catheter connection port 46, as shown in FIG. 2. In some examples, the advantages associated with controlling different fluid pathways in IMD 12 can be realized when valve 36 is arranged in a different location of IMD 12 than the location in the example of FIG. 2. In one example, IMD 12 may include multiple fluid delivery pumps 32, and valve 36 may control fluid pathways to and/or from the multiple pumping mechanisms. In another example, IMD 12 may include multiple fluid reservoirs 34, and valve 36 may control fluid pathways to and/or from the multiple reservoirs 34 to control internal fluid transfer within IMD 12. In some examples, IMD 12 may include multiple injection ports, e.g., multiple catheter connection ports 46 connected to multiple catheters 18 or a single catheter connection port 46 connected to a multi-lumen catheter 18. In these example, IMD 12 may include valve 36 interposed between fluid delivery pump 32 and catheter connection port 46 to control different fluid lumens leading to patient 16. Additionally, positioning valve 36 between fluid delivery pump 32 and catheter connection port 46 enables IMD 12 to control fluid pressure within catheter 18, e.g., by closing or partially closing valve 36 to reduce fluid flow and pressure in catheter 18. In some examples, valve 36 allows catheter pressure to be maintained below a preset upper limit. Whatever the particular fluid pathway configuration, valve 36 may be employed to handle fluid routing and control issues within IMD 12.

IMD 12 may include multiple controllable valves 36 arranged in different locations within IMD 12. For example, IMD 12 may include valve 36 and another controllable valve arranged adjacent to catheter connection port 46. The controllable valves may be used to create a closed recirculation loop in IMD 12 that includes fluid delivery pump 32, fluid pathway 48, catheter access fluid pathway 40, valve 36, reservoir fluid pathway 38, and reservoir 34. A recirculation loop may be used, e.g., to keep components wetted and to keep fluid delivery pump 32 moving during storage and transport of IMD 12.

Valve 36 is configured to electromechanically actuate in response to instructions from processor 26. In one example, valve 36 includes an actuator, such as a pneumatic actuator, electrical actuator, hydraulic actuator, or the like. In another example, valve 36 includes a solenoid, piezoelectric element, or similar features to convent electrical energy into mechanical energy to mechanically open and close valve 36. Valve 36 may include a limit switch, proximity sensor, or other electromechanical device to provide confirmation that valve 36 is in an open or closed position.

During operation of IMD 12, valve 36 may default to a normally closed position, thereby closing access to both reservoir fluid pathway 38 and catheter access fluid pathway 40. When closed, valve 36 provides an additional mechanical barrier beyond septum 44 to block fluid exchange between reservoir 34 and an environment surrounding IMD 12, such as a subcutaneous pocket of patient 16. In examples where reservoir 34 is pressurized, fluid pressure generally only biases against septum 44 during a refill operation, when valve 36 is actuated to open reservoir fluid pathway 38. Accordingly, accidental impingement of septum 44 does not release fluid from reservoir 34 during normal operation of IMD 12.

Periodically, fluid may need to be percutaneously added or withdrawn from IMD 12. Fluid may need to be withdrawn from reservoir 34 if a clinician wishes to replace an existing fluid with a different fluid or a similar fluid with different concentrations of therapeutic agents. Fluid may also need to be added to reservoir 34 if all therapeutic fluid has been or will be delivered to patient 16. Additionally, a clinician may need direct fluid access to catheter 18, e.g., through catheter access pathway 40. Direct catheter access (i.e., access that bypasses reservoir 34 and fluid delivery pump 32) may be used to provide a direct fluid bolus to patient 16, such as direct injection of therapeutic fluid or a direct injection of a dye for dye study testing. Direct catheter access may also be used to remove fluid from patient 16 for testing or analysis. In one example, cerebrospinal fluid may be removed from patient 16 when catheter 18 is implanted in an epidural space.

Inlet port 42 provides access for adding or withdrawing fluid from IMD 12 through septum 44. Accordingly, inlet port 42 is located on a peripheral surface of a housing of IMD 12 and is in fluid communication with valve 36. Inlet port 42 may define an access aperture for percutaneously accessing septum 44. Septum 44 may be a self-sealing member, e.g., a deformable biocompatible polymer, that prevents loss of therapeutic fluid delivered to reservoir 34 via inlet port 42. Septum 44 is accessible using a percutaneous delivery system, e.g., a hypodermic syringe with a needle configured to penetrate septum 44. Septum 44 may seal shut when the needle is removed from inlet port 42.

Processor 26 of IMD 12, alone or in conjunction with a processor of programmer 20 or another device communicatively connected to IMD 12, may be configured to control actuation of valve 36 to control access to reservoir fluid pathway 38 and catheter access fluid pathway 40 through inlet port 42. In one example, processor 26 receives instructions, e.g., from a user via programmer 20, to open reservoir fluid pathway 38. Processor 26 actuates valve 36 to open reservoir fluid pathway 38, allowing a user (e.g., patient or clinician) to percutaneously penetrate septum 44 and transfer fluid through valve 36 into reservoir 34. Processor 26 actuates valve 36 to close reservoir fluid pathway 38 after reservoir 34 is suitably filled, e.g., upon receiving an indication from a user via programmer 20 or upon receiving and analyzing a signal from sensor 50 indicating that reservoir 34 is full or that fluid is no longer passing through inlet port 42. In another example, processor 26 receives instructions, e.g., from a user via programmer 20, to open catheter access fluid pathway 40. Processor 26 actuates valve 36 to open catheter access fluid pathway 40, allowing a user to percutaneously penetrate septum 44 and transfer fluid through valve 36 and catheter 18.

In general, memory 28 stores program instructions and related data that, when executed by processor 26, cause IMD 12 and processor 26 to perform the functions attributed to them in this disclosure. For example, memory 28 of IMD 12 may store instructions for execution by processor 26 including, e.g., therapy programs, programs for actuating valve 36, programs for monitoring and comparing a signal generated by sensor 50, and any other information regarding therapy delivered to patient 16 and/or the operation of IMD 12. Memory 28 may include separate memories for storing instructions, patient information, therapy parameters, therapy adjustment information, program histories, and other categories of information such as any other data that may benefit from separate physical memory modules. Therapy adjustment information may include information relating to timing, frequency, rates and amounts of patient boluses or other permitted patient modifications to therapy.

In some examples, processor 26 of IMD 12 may collect and store measurements made by sensor 50 in memory 28 and/or in a memory associated with an external device communicatively coupled to IMD 12, such as programmer 20. As further described below with respect to FIG. 9, sensor 50 may be configured in some examples to detect user access of inlet port 42. In some examples, sensor 50 is configured to detect a fluid characteristic including, e.g., fluid flow, through at least one of inlet port 42, fluid delivery pump 32, or catheter connection port 46. Accordingly, a memory may store data that includes, e.g., a time and date stamp when inlet port 42 is accessed with a delivery system, data corresponding to fluid filling or withdrawal rates through inlet port 42, data corresponding to fluid filling rates or withdrawal rates from reservoir 34, data corresponding to a fluid volume in reservoir 34 at various times, data corresponding to fluid rates through catheter connection port 46, or data corresponding to a final fluid volume in reservoir 34 during different steps of a reservoir refilling procedure.

With knowledge of these data, IMD 12 or another external device communicatively coupled to IMD 12, may periodically evaluate the efficacy of therapeutic fluid delivery through IMD 12. In one example, IMD 12 analyzes a fluid characteristic sensed via sensor 50 to determine the chemical composition of fluids delivered through IMD 12. IMD 12 can identify therapeutic fluids inappropriate for a specific patient 16, e.g., not prescribed or not programmed into memory 28. IMD 12 can also take corrective action including, e.g., transmitting a message to programmer 20 or terminating fluid delivery though fluid delivery pump 32. In another example, IMD 12 can trace fluid flows entering and exiting IMD 12 to determine the fluid integrity of IMD 12. By storing and analyzing sensor data, IMD 12 may provide a clinician with closed-loop feedback indicative of the utilization of IMD 12 and the efficacy of therapy delivered via IMD 12.

At various times during the operation of IMD 12 to treat patient 16, communication to and from IMD 12 may be necessary to, e.g., control actuation of valve 36 to permit fluid flow through reservoir fluid pathway 38 or catheter access pathway 40, change therapy programs, adjust parameters within one or more programs, configure or adjust a particular bolus, or to otherwise download information to or from IMD 12. Processor 26 controls telemetry module 30 to wirelessly communicate between IMD 12 and other devices including, e.g. programmer 20. Telemetry module 30 in IMD 12, as well as telemetry modules in other devices described in this disclosure, such as programmer 20, can be configured to use, e.g., RF communication techniques and/or near field communication techniques to wirelessly send and receive information to and from other devices respectively according to standard or proprietary telemetry protocols. In addition, telemetry module 30 may communicate with programmer 20 via proximal inductive interaction between IMD 12 and the external programmer. Telemetry module 30 may send information to external programmer 20 on a continuous basis, at periodic intervals, or upon request from the programmer.

Power source 44 delivers operating power to various components of IMD 12. Power source 44 may include a rechargeable battery or non-rechargeable battery and a power generation circuit to produce the operating power. In the case of a rechargeable battery, recharging may be accomplished through a variety of techniques including, e.g., proximal inductive interaction or kinetic energy-scavenging device. As another alternative, an external inductive power supply can transcutaneously power IMD 12 as needed or desired.

Figure 3:
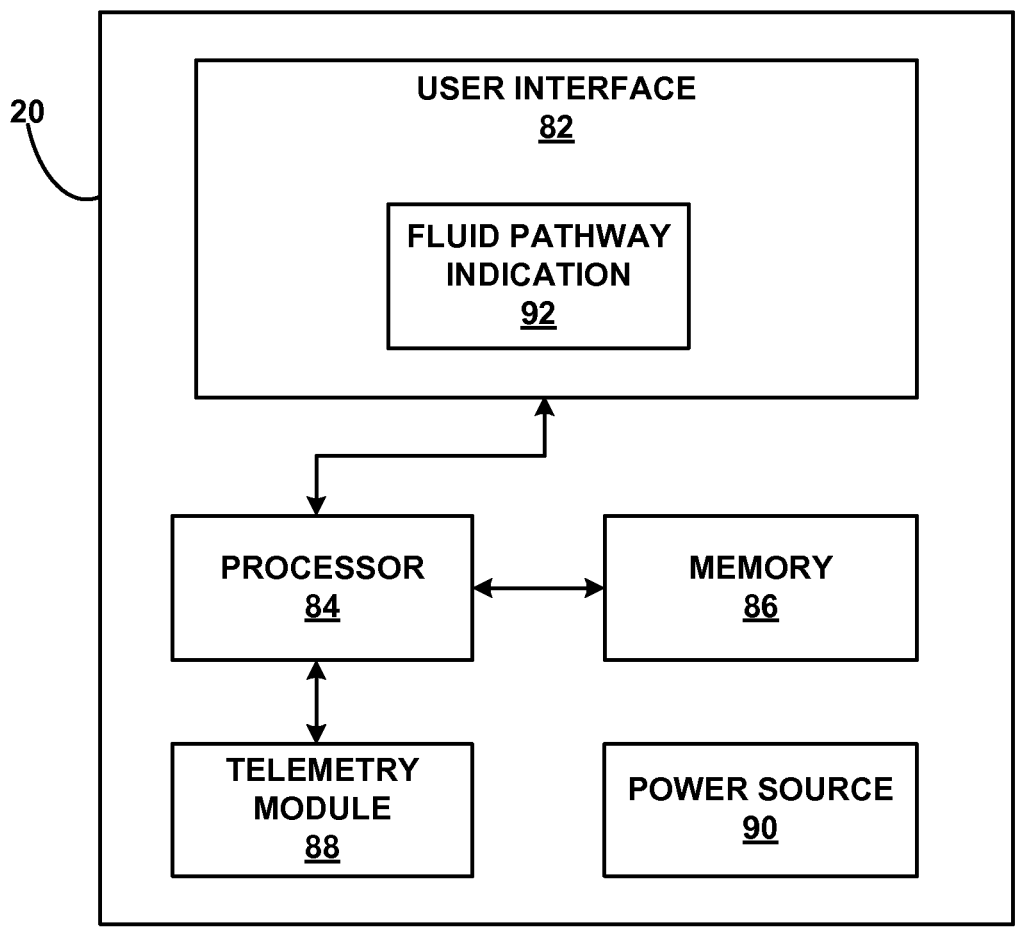
FIG. 3 is a functional block diagram illustrating an example of an external programmer shown in FIG. 1.

As described, IMD 12 may communicate with one or more external devices at various times during the operation of IMD 12. In the example of FIG. 1, IMD 12 communicates with external programmer 20. FIG. 3 is a functional block diagram illustrating an example of various components of external programmer 20. As shown in FIG. 3, external programmer 20 may include user interface 82, processor 84, memory 86, telemetry module 88, and power source 90. A clinician or patient 16 interacts with user interface 82 to control actuation of valve 36, change the parameters of a therapy program, change therapy programs within a group of programs, view therapy information, view historical or establish new therapy programs, or otherwise communicate with IMD 12 or view or edit programming information. Processor 84 controls user interface 82, retrieves data from memory 86 and stores data within memory 86. Processor 84 also controls the transmission of data through telemetry module 88 to IMD 12. The transmitted data may include, e.g., instructions to control actuation of valve 36 to open or close reservoir fluid pathway 38 and/or catheter access fluid pathway 40. The transmitted data may also include therapy program information specifying various therapeutic fluid delivery parameters. For example, in cases where IMD 12 includes multiple fluid reservoirs, transmitted data may specify a reservoir or sequence of reservoirs, e.g., by specifying reservoir discharge valve actuation commands, to enable fluid delivery pump 32 to deliver fluids from one or more reservoirs. Memory 86 may store, e.g., operational instructions for processor 84 and data related to therapy for patient 16.

Programmer 20 may be a hand-held computing device that includes user interface 82 that can be used to provide input to programmer 20. User interface 82 may generally include a display screen or other output media, and user input media. User interface 82 may be configured to present therapy program information to the user as graphical bar graphs or charts, numerical spread sheets, or in any other manner in which information may be displayed. In addition, user interface 82 may be configured to present inlet port information, valve information, fluid pathway information, reservoir information, pump information, refill information, or the like to the user in text or graphical display form. The information may generally indicate, e.g., that an inlet port is being accessed by a delivery system, a valve is actuated to specific position, a fluid pathway is open or closed, a reservoir is filling or discharging, or that a pump is operating. In some examples, the information includes operating statistics including, e.g., flow rates, pressures, temperatures, volumes, time stamps, or the like.

In one example, user interface 82 may display a visual graphical representation of inlet port 42, valve 36, reservoir fluid pathway 38, and catheter access fluid pathway 40. Portions of the visual graphic may change color, shape, size, or the like to, e.g., indicate the position of valve 36, whether fluid pathway 38 or 40 is opened or closed, or whether fluid is passing through inlet port 42 as indicated by data from sensor 50. In some further examples, user interface 82 may present nominal or suggested therapy parameters that the user may accept via user interface 82. User interface 82 also provides input mechanisms to enable the user to program IMD 12 in accordance with one or more therapy programs or otherwise provide data to IMD 12 necessary for delivering therapy to patient 16.

When programmer 20 is configured for use by a clinician, user interface 82 may be used to transmit initial programming information to IMD 12 including hardware information for system 10, e.g. the number of reservoirs 34, the number of fluid delivery pumps 32, the type of valve 36, the types of fluid pathways connecting to valve 36, the type of catheter 18, the position of catheter 18 within patient 16, a baseline orientation of at least a portion of IMD 12 relative to a reference point, and software information related to therapy delivery and operation of IMD 12, e.g. parameters for controlling valve 36, therapy parameters of therapy programs stored within IMD 12 or within programmer 20, the type and amount, e.g., by volume of therapeutic fluid(s)

delivered by IMD 12 and any other information the clinician desires to program into IMD 12.

When configured as a clinician programmer, programmer 20 may transmit an identification number, authorization code, or like identifying information via telemetry module 88 to IMD 12 to authenticate that programmer 20 is a clinician programmer. Alternatively, processor 84 of programmer 20 may prompt a user to enter a clinician access code via user interface 82. Regardless of the authorization technique, verification of clinician authority may be required when programmer 20 is configured as a clinician programmer. A clinician programmer may permit a user to manipulate features of IMD 12 that a user cannot manipulate using a corresponding patient programmer. In one example, a clinician programmer can control actuation of valve 36 to access reservoir fluid pathway 38 or catheter access fluid pathway 40, while a corresponding patient programmer is not authorized to control actuation of valve 36. In this manner, a therapy delivery system that includes IMD 12 and programmer 20 can limit access to controlled substances (e.g., morphine) in reservoir 34 via fluid reservoir pathway 38. Further, restricting refilling to a clinician programmer may reduce refilling mistakes, e.g., delivering fluid through inlet port 42 to the wrong reservoir in a multi-reservoir IMD or delivering fluid to catheter access fluid pathway 40 instead of reservoir fluid pathway 38.

As described, programmer 20 may also be configured for use by patient 16. When configured as a patient programmer, programmer 20 may have limited functionality in order to prevent patient 16 from altering critical functions or applications that may be detrimental to patient 16. Accordingly, programmer 20 may only allow patient 16 to adjust certain therapy parameters or set an available range for a particular therapy parameter. In one example, programmer 20 may only allow patient 16 to control actuation of valve 36 to access reservoir 34 at certain time intervals, e.g., to prevent repeated refilling of reservoir 34 at a rate that indicates patient 16 is over medicating. In another example, programmer 20 may only allow patient 16 to control actuation of valve 36 to access reservoir 34 when sensor 50 indicates that reservoir 34 is empty or will be empty shortly based on fluid delivery rates. In this manner, programmer 20 can prevent patient 16 from mixing incompatible drugs in reservoir 34. In another example, programmer 20 may allow patient 16 to access one or more reservoirs while preventing patient 16 from accessing another one or more different reservoirs, e.g., based on the type of therapeutic fluid housed in each specific reservoir. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered, when IMD 12 needs to be refilled or when the power source within programmer 20 or IMD 12 need to be replaced or recharged.

In the example of FIG. 3, user interface 82 of programmer 20, whether employed as a patient or clinician programmer, includes fluid pathway indication 92. Fluid pathway indication 92 is configured to indicate whether at least one of fluid pathway 38, 40 of IMD 12 is opened or closed. Fluid pathway indication 92 may include any combination of textual or graphical representations of reservoir fluid pathway 38 and catheter access fluid pathway 40. For example, fluid pathway indication 92 may include icons representative of valve 36, reservoir fluid pathway 38, and/or catheter access fluid pathway 40. The icons may be colored, filled in, highlighted, increase and decrease in size, or otherwise vary based, e.g., on the position of valve 36, whether reservoir fluid pathway 38 and/or catheter access fluid pathway 40 is opened or closed, or whether fluid is traversing through reservoir fluid pathway 38 and/or catheter access fluid pathway 40. In another example, fluid pathway indication 92 may include a textual indication of the position of valve 36, e.g., identifying that valve 36 is closed or that either reservoir fluid pathway 38 or catheter access fluid pathway 40 is open.

As described, processor 26 of IMD 12 may collect and store measurements made by sensor 50 in memory 28. An external instrument, e.g., a patient programmer, may automatically pull measurements made by sensor 50 from memory 28 via telemetry modules 30 and 88 on a regular basis. In another example, a clinician programmer may pull measurements made by sensor 50 from memory 28 via telemetry modules 30 and 88 on a patient visit. In either case, processor 84 may store the measurements made by sensor 50 in memory 86 and may employ measurements made by sensor 50 to analyze the utilization of IMD 12 and the efficacy of therapy delivered via IMD 12. Further, while various data may be stored in memory 86 during the operation of IMD 12, in other examples, data may be streamed, e.g., continuously or upon request, to an external instrument without being stored in memory 86.

Telemetry module 88 allows the transfer of data to and from programmer 20 and IMD 12, as well as other devices, e.g. according to the RF communication techniques described above with reference to FIG. 2. Power source 90 may be a non-rechargeable battery or a rechargeable battery, such as a lithium ion or nickel metal hydride battery. In some examples, programmer 20 may be configured to recharge IMD 12 in addition to programming IMD 12.

Figure 4:
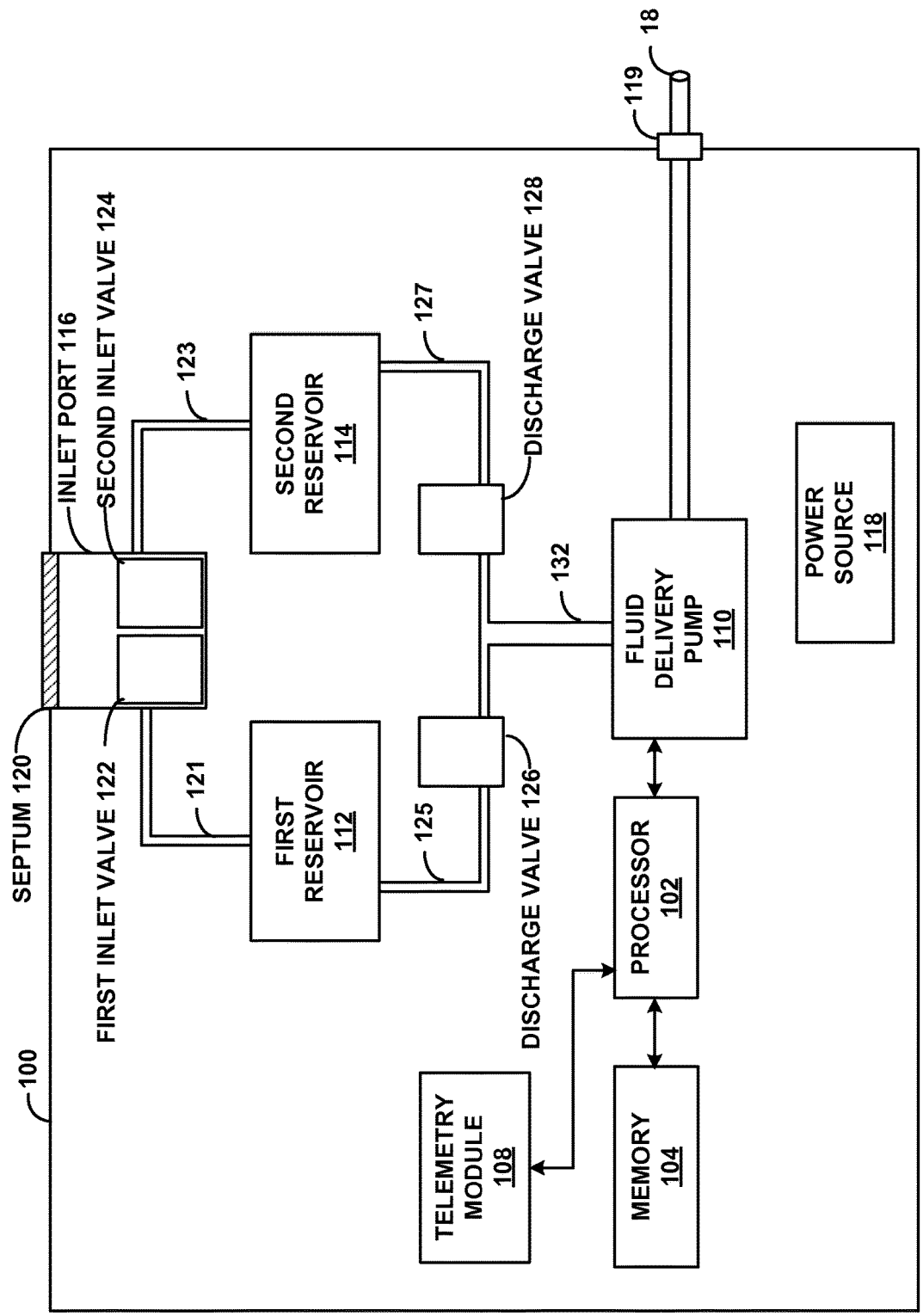
FIG. 4 is a functional block diagram illustrating an example of an alternative implantable fluid delivery device.

FIG. 4 is a functional block diagram illustrating components of an example of IMD 100 with two fluid reservoirs 112, 114. IMD 100 may be implanted in patient 16 in addition to, or in lieu of, IMD 12. IMD 100 may correspond substantially to IMD 12 (FIGS. 1 and 2) and may communicate with programmer 20 (FIGS. 1 and 3). IMD 100 includes processor 102, memory 104, telemetry module 108, fluid delivery pump 110, first reservoir 112, second reservoir 114, inlet port 116, power source 118, and catheter connection port 119 which connects to catheter 18. Inlet port 116 includes septum 120, first inlet valve 122, and second inlet valve 124. First inlet valve 122 connects to first reservoir 112 through first reservoir fluid fill pathway 121, which extends from first inlet valve 122 to first reservoir 112. Fluid delivery pump 110 is connected to first reservoir 112 through first reservoir fluid discharge pathway 125, first reservoir discharge valve 126, and fluid pathway 132. Second inlet valve 124 connects to second reservoir 114 through second reservoir fluid fill pathway 123, which extends from second inlet valve 124 to second reservoir 114. Fluid delivery pump 110 is connected to second reservoir 114 through second reservoir fluid discharge pathway 127, second reservoir discharge valve 128, and fluid pathway 132.

IMD 100 also includes processor 102, which is configured to control various components of IMD 100 with the aid of instructions, e.g., stored in memory 108 or communicated to IMD 100 via telemetry module 108. Processor 102 is communicatively connected to memory 104, telemetry module 108, and fluid delivery pump 110. Though not shown, processor 102 is also communicatively connected to first inlet valve 122, second inlet valve 124, first reservoir discharge valve 126, and second reservoir discharge valve 128, to control the opening and closing of valves 122, 124, 126, and 128.

In general, the components and operation of IMD 100 may correspond to the description of the components and operation of IMD 12 (FIGS. 1 and 2). For example, valves 122, 124, 126, and 128 may actuate open and closed according to instructions communicated from processor 102, similar to the operation of valve 36 in IMD 12 according to instructions communicated from processor 26. In some examples, IMD 100 may include a catheter access fluid pathway similar to catheter access fluid pathway 40 in IMD 12 for providing a clinician direct access to catheter 18, e.g., to extract fluid through catheter 18 or to provide a fluid bolus to patient 16. In some examples, IMD 100 may include more than two reservoirs 112, 114 (e.g., three, four, five) for storing more than two types of therapeutic fluid or for storing different quantities or different concentrations of the same type of therapeutic fluid.

During operation of IMD 100, processor 102 controls fluid delivery pump 110 with the aid of instructions stored in memory 104 to delivery therapeutic fluid from first reservoir 112 and second reservoir 114 to patient 16 via catheter 18. Instructions executed by processor may, e.g., define therapy programs that specify different doses or different types of therapeutic fluid to be delivered to a target therapy site within patient 16. For example, the programs may specify a schedule for delivering a first therapeutic fluid from first reservoir 112 and for delivering a second therapeutic fluid from second reservoir 114. In some examples, the programs may alternate delivery of the first therapeutic fluid from first reservoir 112 and the second therapeutic fluid from second reservoir 114 to achieve an efficacious therapeutic result. For example, first reservoir 112 may contain an antispastic drug such as baclofin while second reservoir 114 may contain a pain reliever such as morphine. Alternatively, the programs may deliver the first therapeutic fluid from first reservoir 112 and the second therapeutic fluid from second reservoir 114 substantially simultaneously, e.g., by allowing mixing in fluid pathway 132 or by delivering time interleaved drug boluses from first reservoir 112 and second reservoir 114.

In the example of FIG. 4, fluid delivery pump 110 delivers fluid through catheter connection port 119 to catheter 18. In some examples, IMD 100 may include more than one fluid delivery pump 110, e.g., to prevent mixing of the fluid in reservoir 112 and the fluid in reservoir 114, to increase fluid delivery rates, to provide substantially simultaneous delivery of different fluids from first reservoir 112 and second reservoir 114 to a target therapy site in patient 16, or to deliver fluids through different lumens of catheter 18 to different target therapy sites. For example, IMD 100 may include a first fluid delivery pump that draws fluid from first reservoir 112 and pumps the fluid to catheter 18 and a second fluid delivery pump that draws fluid from second reservoir 114 and pumps the fluid to catheter 18. The first fluid delivery pump and second delivery pump may operate substantially simultaneously or separately, e.g., at different times or different durations. In another example, IMD 100 may include a first fluid delivery pump that draws fluid from first reservoir 112 and pumps the fluid to catheter 18 while a second fluid delivery pump draws fluid from second reservoir 114 and pumps the fluid to a separate catheter. In this manner, IMD 100 can provide dedicated fluid delivery pathways from first reservoir 112 and second reservoir 114 to one or more target therapy sites in patient 16.

In response to therapy programs stored on memory 104 or instructions communicated through telemetry module 108, processor 102 may selectively control actuation of first reservoir discharge valve 126 and/or second reservoir discharge valve 128 to the control the selection and delivery of fluid through fluid delivery pump 110 to catheter 18. In one example, processor 102 controls actuation of first reservoir discharge valve 126 to an open position while second reservoir discharge valve 128 is in a closed position. First reservoir discharge pathway 125 is placed in fluid communication with first reservoir 112, allowing fluid delivery pump 110 to delivery fluid from first reservoir 112 to patient 16. In another example, processor 102 controls actuation of both first reservoir discharge valve 126 and second reservoir discharge valve 128 to open positions, placing first reservoir discharge pathway 125 and second reservoir discharge pathway 127 in fluid communication with first reservoir 112 and second reservoir 114, respectively. In this manner, IMD 100 facilitates fluid mixing in fluid pathway 132 and fluid delivery pump 110 prior to delivering a fluid bolus to patient 16. Additionally, in some examples, processor 102 may control actuation of first reservoir discharge valve 126 and second reservoir discharge valve 128 to selectively mix different amount of fluid from first reservoir 112 and second reservoir 114, respectively. For example, processor 102 may alternately open and close first reservoir discharge valve 126 and second reservoir discharge valve 128, or open first reservoir discharge valve 126 and second reservoir discharge valve 128 different amounts, to achieve different mixing ratios.

In general, therapeutic fluids housed in first reservoir 112 and second reservoir 114 may be the same as the therapeutic fluids housed in reservoir 34 (FIG. 2). That is, first reservoir 112 may house a first therapeutic fluid and second reservoir 114 may house a second therapeutic fluid that are the same therapeutic fluid, e.g., in different quantities or different concentrations, to provide therapy dosing flexibility. Alternatively, first reservoir 112 may house a first therapeutic fluid and second reservoir 114 may house a second therapeutic fluid that are different therapeutic fluids, e.g., to achieve different therapeutic effects or to provide different fluid storage conditions, such as acidic and basic pH storage conditions. In some examples, IMD 100 may include more than two reservoirs, e.g., three, four, five, or more reservoirs, to provide a user with flexibility to house different fluids in different reservoirs.

First reservoir 112 and second reservoir 114 are generally sized to house enough fluid to allow patient 16 to receive therapeutic dosing without continuously refilling first reservoir 112 and second reservoir 114. In some examples, first reservoir 112 and second reservoir 114 are each sized based, e.g., on the shelf-life of the fluid expected to be housed in reservoir 112, 114, the anticipated delivery rate of the fluid expected to be housed in reservoir 112, 114, or to control the size and weight of IMD 100. In one example, first reservoir 112 and second reservoir 114 each house between approximately 5 milliliters and approximately 120 milliliters, such as between approximately 15 milliliters and approximately 75 milliliters. In some examples, first reservoir 112 and second reservoir 114 are the same size. In other examples, first reservoir 112 and second reservoir 114 are different sizes. In this manner, IMD 100 may be configured to house different fluid volumes in different reservoirs, giving a user flexibility to store therapeutic fluids in varying quantities.

In general, first reservoir 112 and second 114 may be arranged in numerous locations within IMD 100 including, e.g., a stacked arrangement or a coplanar arrangement to minimize the overall thickness of IMD 100. In one example, a coplanar arrangement is a side-by-side arrangement where first reservoir 112 is positioned side-by-side with second reservoir 114, as in the example of FIG. 4. In another example, first reservoir 112 is separated from second reservoir 114, e.g., by IMD 100 hardware, in a coplanar arrangement. In alternative examples, first reservoir 112 and second reservoir 114 are stacked. That is, first reservoir 112 is positioned above second reservoir 114. In some examples, first reservoir 112 is positioned directly above second reservoir 114. In other examples, first reservoir 112 is laterally displaced from second reservoir 114.

In general, memory 104 of IMD 100 or memory 86 of programmer 20 stores program instructions that control actuation of first reservoir discharge valve 126 and second reservoir discharge valve 128. In some examples, valve actuation instructions include instructions that define a therapy program or therapy program group for delivering therapy to patient 16. When executed by processor 102, e.g., while processor 102 simultaneously controls fluid delivery pump 110, valve actuation instructions selectively open and close at least one of first reservoir discharge pathway 125 and second reservoir discharge pathway 127. In this manner, fluid may be selectively delivered from at least one of first reservoir 112 or second reservoir 114 in IMD 12.

Regular access to first reservoir fluid fill pathway 121 and second reservoir fluid fill pathway 123 is generally necessary, e.g., to refill reservoirs 112, 114 with therapeutic fluids currently housed in reservoirs 112, 114, or to withdraw therapeutic fluids currently housed in reservoirs 112, 114 for replacement with different therapeutic fluids or similar therapeutic fluids in different concentrations. In some examples, programmer 20, whether configured as a patient programmer or clinician programmer, is configured to communicate instructions to IMD 100 to selectively control actuation of valves 122, 124 to permit refill to or withdrawal from reservoirs 112, 114. According to one example, a user may enter a valve actuation command in user interface 82 of programmer 20 (FIG. 3) to access reservoirs 112, 114. Process 84 of programmer 20 may transmit instructions via telemetry modules 82 and 108 to IMD 100 based on the received user input. In turn, processor 102 of IMD 100 may receive the instructions and transmits instructions for one of valves 122 or 124 to actuate, thereby opening a fluid pathway for refilling or withdrawing from first reservoir 112 or second reservoir 114. A user may subsequently penetrate septum 120 by, e.g., inserting a hypodermic needle through septum 120. The user may then add fluid into the open fluid pathway or withdraw from the open fluid pathway. When the refilling operation is completed, processor 102 may actuate the opened valve 122 or 124 closed, e.g., upon receiving instructions via telemetry modules 82 and 108 via programmer 20.

In some examples, processor 102 closes the opened valve 122 or 124 in response to receiving and analyzing a signal from a sensor (not shown). In one example, processor 102 detects when a delivery needle is inserted or withdrawn from inlet port 116 based on sensor data, and processor 102 closes valve 122 or 124 when the needle is withdrawn from inlet port 116. In another example, a sensor detects fluid movement through inlet port 116, and processor 102 closes valve 122 or 124 when the sensor ceases to detect fluid movement through inlet port 116. In a further example, a sensor detects a fluid volume, e.g., through pressure, in reservoir 112 and 114, and processor 102 closes valve 122 or 124 when a fluid volume in reservoir 112 and 114 is no longer changing. IMD 100 may also employ a combination of these different examples.

Figure 5:
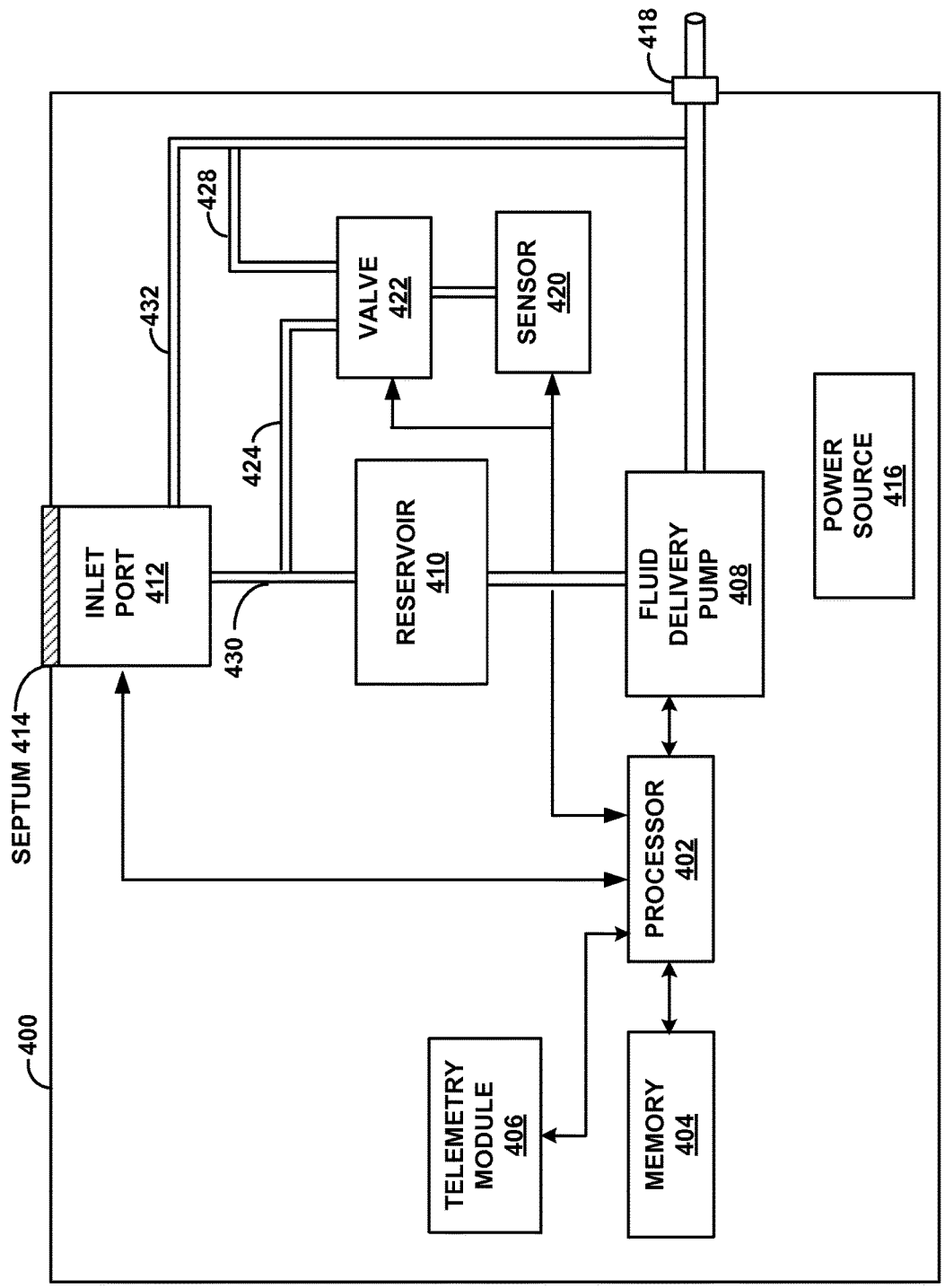
FIG. 5 is a functional block diagram illustrating another example alternative implantable fluid delivery device.

In view of the advantages of using a controllable valve in a device that includes multiple fluid pathways, other fluid delivery devices according to this disclosure may have at least one controllable valve interposed between different fluid pathways in addition to, or instead of, at an inlet port. FIG. 5 is a functional block diagram illustrating components of an example of IMD 400, which includes processor 402, memory 404, telemetry module 406, fluid delivery pump 408, reservoir 410, inlet port 412, septum 414, power source 416, catheter connection port 418, sensor 420, valve 422, reservoir sensor fluid pathway 424, and catheter access sensor fluid pathway 428. Processor 402 is communicatively connected to memory 404, telemetry module 406, fluid delivery pump 408, sensor 420, and valve 422. Fluid delivery pump 408 is connected to reservoir 410 and catheter connection port 418. Reservoir sensor fluid pathway 424 is connected fluid pathway 430, which connects inlet port 412 to reservoir 410. Catheter access sensor fluid pathway 428 is connected to fluid pathway 432, which connects inlet port 412 to catheter connection port 418.

In general, the components and operation of IMD 400 may correspond to the description of the components and operation of IMD 12 and 100 (FIGS. 2 and 4). For example, IMD 400 is configured to communicate with an external device including, e.g., programmer 20, to transmit information or to download information to or from IMD 400. In another example, valves 422 actuates open and closed according to instructions communicated from processor 402, similar to the operation of valve 36 in IMD 12 and valves 122, 124, 126, and 128 in IMD 100.

It may be useful for the efficient operation of IMD 400 if IMD 400 includes means for identifying different fluid movements within IMD 400. In some examples, IMD 400 includes different sensors that are arranged to connect to different reservoirs or fluid pathways in IMD 400 including, e.g., reservoir 410, fluid pathway 430, fluid pathway 432, or a fluid pathway in fluid communication with the discharge of fluid delivery pump 408. However, in additional examples, IMD 400 may reduce sensor requirements by fluidly connecting multiple fluid pathways 424, 428 to sensor 420 via valve 422, as shown in FIG. 5.

At various times during the operation of IMD 400, processor 402 may control actuation of valve 422 to place either reservoir sensor fluid pathway 424 or catheter access sensor fluid pathway 428 in fluid communication with sensor 420. Sensor 420 measures a fluid characteristic, e.g., upon querying by processor 402, and transmits the measured fluid characteristic data to processor 402, e.g., to be streamed to programmer 20 or for analysis and/or storage in memory 404. In some examples, processor 402 executes instructions to repeatedly actuate valve 422 to alternately place reservoir sensor fluid pathway 424 and catheter access sensor fluid pathway 428 in fluid communication with sensor 420. In one example, processor 402 actuates valve 422 according to the configuration of inlet port 412. That is, valve 422 opens catheter access sensor fluid pathway 428 when inlet port 412 is configured to direct fluid through pathway 432, but valve 422 opens reservoir sensor fluid pathway 424 when inlet port 412 is configured to direct fluid through pathway 430. Regardless of the specific actuation scheme, valve 422 can be actuated to separately measure a fluid characteristic in each of a plurality of different fluid pathways, thus reducing the number of sensors in IMD 400 and mitigating inconsistencies, e.g., calibration inconsistencies, different sensors may exhibit.

Processor 402 may transmit the measured fluid characteristic data, or data based on analysis of the measured fluid characteristic data, to an external device, e.g., via telemetry module 406. The external device may then process the data, display the data, provide a user prompt, or generally perform any other function attributed to external devices in this disclosure.

In the example of FIG. 5, sensor 420 measures at least one characteristic of a fluid. In various examples, sensor 420 is configured to measure pressure, temperature, pH, electrolytic content, and the like. In some examples, sensor 420 is configured to measure a plurality of fluid characteristics (e.g., two, three, four characteristics). In some examples, IMD 400 includes more than one sensor 420, e.g., to measure in different physical locations of IMD 400.

While sensor 420 is arranged for fluid communication with reservoir sensor fluid pathway 424 and catheter access sensor fluid pathway 428, in general, sensor 420 can be configured for fluid communication with any fluid pathways in IMD 400. In some examples, IMD 400 includes a plurality of reservoirs and sensor 420 is configured to fluidly communicate with each of the reservoirs, or fluid pathways to or from each of the reservoirs, through valve 422. In some examples, IMD 400 includes a plurality of pumps and sensor 420 is configured to fluidly communicate with fluid pathways to and/or from each of the pumps through valve 420.

As described, IMD 12 (FIG. 2), IMD 100 (FIG. 4), and IMD 400 (FIG. 5) include at least one controllable valve for opening or closing at least one fluid pathway. Example valves configured for use in a fluid delivery device, such as IMD 12, 100, 400, are described in greater detail with reference to FIGS. 6, 7A-B, and 9.

Figure 6:
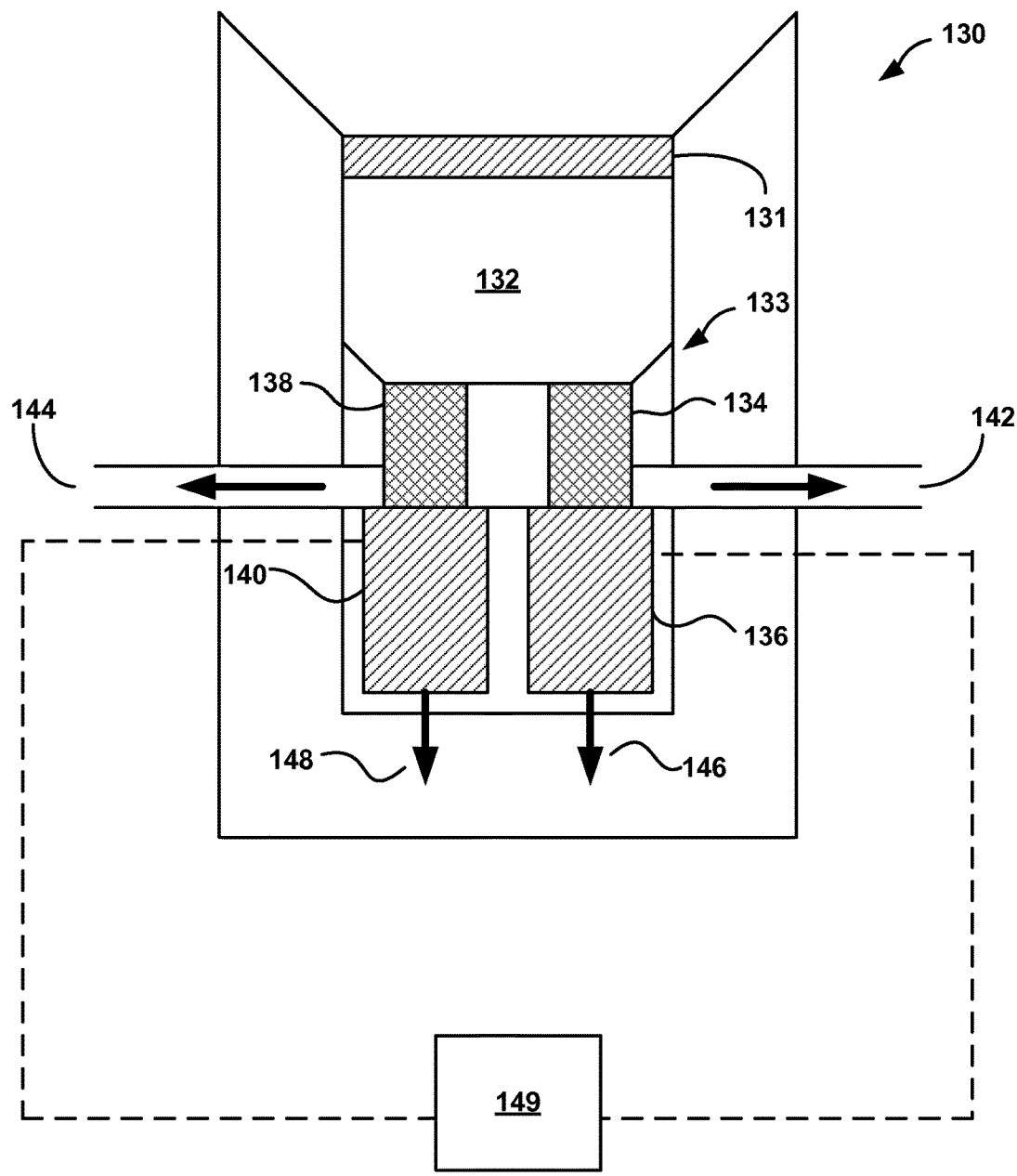
FIG. 6 is a conceptual diagram illustrating an example valve for an implantable fluid delivery device.

FIG. 6 is a conceptual diagram illustrating an example inlet port 130 with valve 133 for use in IMD 12, 100, 400. As shown in FIG. 6, inlet port 130 defines refill aperture 132 which is accessible, e.g., with a percutaneous delivery system, through septum 131. Valve 133 is in fluid communication with refill aperture 132. Valve 133 includes first valve piston 134 connected to first actuator 136. Valve 133 also includes second valve piston 138 connected to second actuator 140. First valve piston 134 actuates in the direction indicated by arrow 146 to open or close fluid pathway 142. Second valve piston 138 actuates in the direction indicated by arrow 148 to open or close fluid pathway 144. Processor 149 is communicatively connected to first actuator 136 and second actuator 140.

During operation, processor 149 controls first actuator 136 and second actuator 140, e.g., with the aid of instructions stored in memory or commands received from programmer 20 to selectively open and close fluid pathways 142, 144. In this manner, an IMD with valve 133 exhibits selectable, controllable fluid pathway access. In one example, fluid pathway 142 extends from valve 133 to catheter connection port 46 (FIG. 2) while fluid pathway 144 extends from valve 133 to fluid reservoir 34 (FIG. 2), thereby providing selectable access to reservoir fluid pathway 38 and catheter access fluid pathway 40. In another example, fluid pathway 142 extends from valve 133 to first fluid reservoir 112 (FIG. 4) while fluid pathway 144 extends from valve 133 to second fluid reservoir 114 (FIG. 4), thereby providing selectable access to first reservoir fluid fill pathway 121 and second reservoir fluid fill pathway 123.

In general, inlet port 130 and valve 133 can be arranged in a number of locations on an IMD including, e.g., such that inlet port 130 is percutaneously accessible on a peripheral surface of an IMD housing. In some examples, valve 133 can be separated from inlet port 130, e.g., to connect fluid pathways that do not require access via inlet port 130. In other words, valve 133 can be connected to fluid pathways that do not extend directly to inlet port 130. For example, valve 133 can be arranged to connect to sensor 420 and multiple fluid pathways in fluid communication with sensor 420, as according to the arrangement of valve 422 in FIG. 5.

Figure 7A:
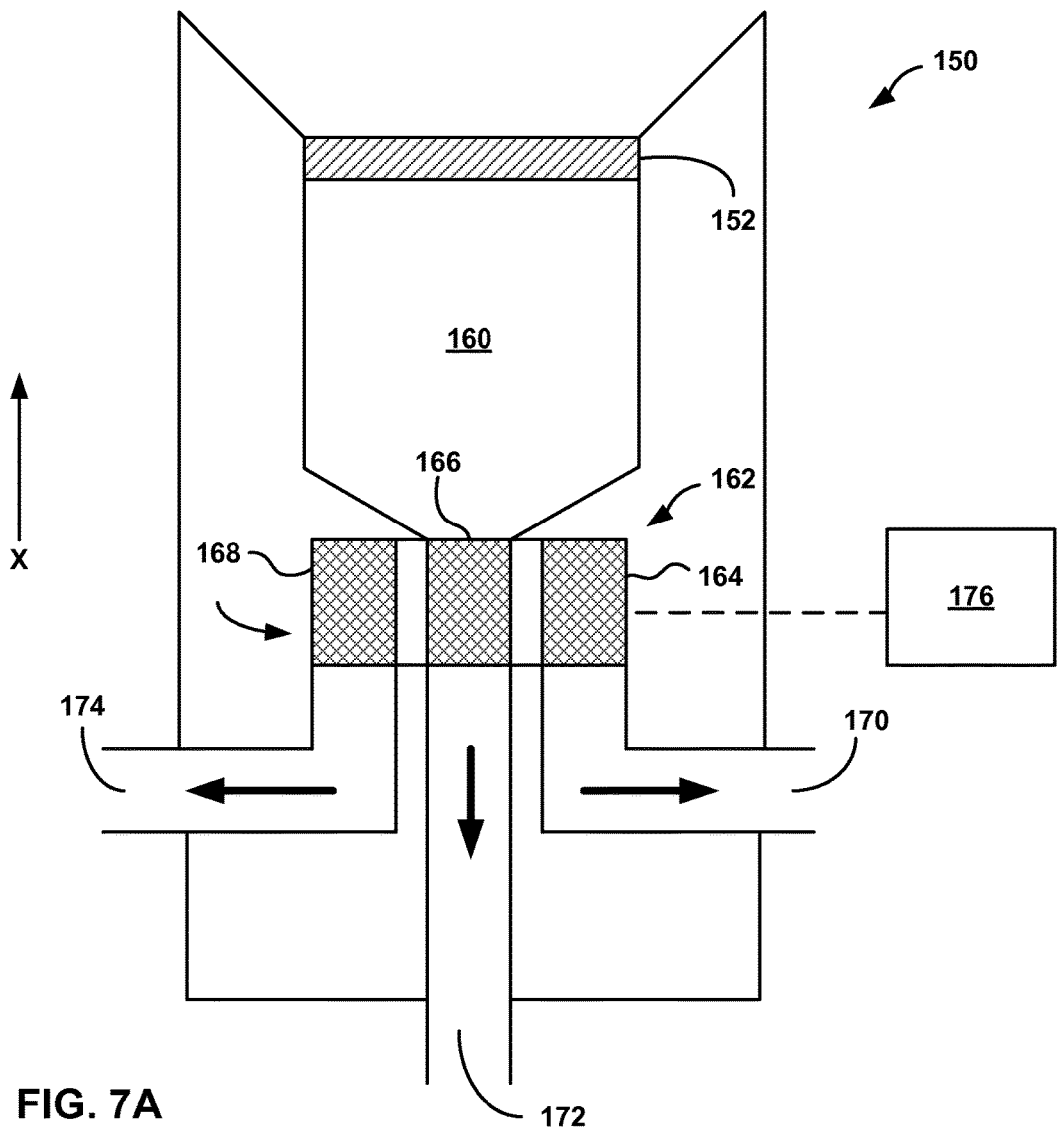
FIGS. 7A and 7B are conceptual cross-sectional and top-view diagrams, respectively, illustrating an example of an alternative valve for an implantable fluid delivery device.

FIG. 7A is a conceptual cross-sectional diagram illustrating an example inlet port 150 with valve 162 for use in IMD 12, 100, 400. As shown in FIG. 7A, inlet port 150 includes inlet aperture 160, which is accessible, e.g., using a percutaneous delivery system, through septum 152. Inlet port 150 is configured for fluid communication with valve 162 and, in particular, a selected one of fluid ports 164, 166, or 168 of valve 162. Fluid ports 164, 166, and 168 are configured to fluidly communicate with fluid pathways 170, 172, and 174, respectively. Valve 162 rotates around a central axis extending in the x-direction indicated on FIG. 7A. As further shown in FIG. 7B, ports 164, 166, and 168 define different openings for conveying fluid through different fluid pathways of valve 162. Valve 162 includes blocking port 180, which is not connected to a fluid pathway but instead serves to block fluid communication through valve 162. Processor 176 is communicatively connected to valve 162.

During operation of valve 162, processor 176, e.g., with the aid of instructions stored in memory or commands received from programmer 20, may rotate valve 162 to place one of ports 164, 166, or 168 in fluid communication with inlet aperture 160. Processor 176 may also rotate valve 162 to expose blocking port 180 to inlet aperture 160, thereby closing valve 162 from fluid communication. Processor 176 may execute instructions to generate signals that are communicated to an intermediate rotating device (not shown) such as an actuator, solenoid, motor, or the like to impart mechanical energy for rotating valve 176.

In some examples, inlet port 150 may include one or more different rotating elements in addition to or in lieu of valve 162. For example, inlet port 150 may include a rotating element interposed between inlet aperture 160 and fluid pathways 170, 172, and 174. The rotating element may rotate instead of valve 162. The rotating element may include a single inlet port (e.g., which may be similar to inlet port 164, 166, or 168) that rotates relative to fluid pathways 170, 172, and 174. When the single inlet port is aligned with one of fluid pathways 170, 172, or 174, fluid communication may be established between inlet aperture 160 and a corresponding one of fluid pathway 170, 172, or 174. The rotating element may also align with blocking port to block fluid communication through inlet aperture 160. The rotating element may be communicatively coupled to processor 176 (e.g., directly or through an intermediary device) and may rotate in response to received instructions.

Figure 7B:
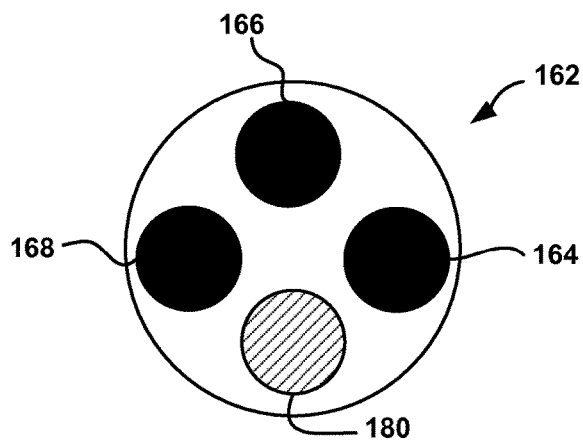

In the example of FIGS. 7A-7B, valve 162 controls fluid communication between inlet aperture 162 and fluid pathways 170, 172, and 174. Fluid is added or withdrawn through valve 162 by penetrating septum 152, e.g., with a percutaneous, hypodermic needle, and rotating valve 162 to expose one of fluid pathways 170, 172, or 174. In one example, fluid pathway 170 connects to a catheter connection port, fluid pathway 172 connects to a first fluid reservoir, and fluid pathway 174 connects to a second fluid reservoir. In another example, fluid pathways 170, 172, and 174 each connect to different reservoirs, e.g., a first reservoir, second reservoir, and third reservoir. In some examples, valve 162 may define a different number of ports 164, 166, 168 and fluid pathways 170, 172, 174, such as the two ports and fluid pathways illustrated with respect to IMD 12, 100.

In general, valve 162 may be separated from inlet port 150 and used in different locations within an IMD, including, e.g., to control fluid delivery from a single fluid pathway to multiple catheters or to control fluid withdrawal from multiple reservoirs to a single fluid delivery pump. In one example, valve 162 is connected to a sensor including, e.g., sensor 420 in FIG. 5. Valve 162 is rotated to expose different fluid pathways 170, 172, 174 to the sensor. As a result, the single sensor is used to measure at least one fluid characteristic in three different pathways, reducing the number of sensor required in IMD 12, 100, 400.

Example valves 36, 122, 124, 133, 162 have generally been described as inlet valves that include at least one fluid pathway connected to at least one fluid reservoir. Further, in some examples, such as IMD 100 in FIG. 4, separate discharge valves 126, 128 control fluid communication between a reservoir and a fluid delivery pump. That is, valves 36, 122, 124, 133, and 162 control fluid pathways for supplying fluid to at least one reservoir, while fluid is drawn from the at least one reservoir through separate fluid pathways for delivery to patient 16. However, in some examples, valves 36, 122, 124, 133, and 162 can function to open or close fluid pathways extending both between an inlet port and a reservoir and between a reservoir and a fluid delivery pump.

Figure 8:
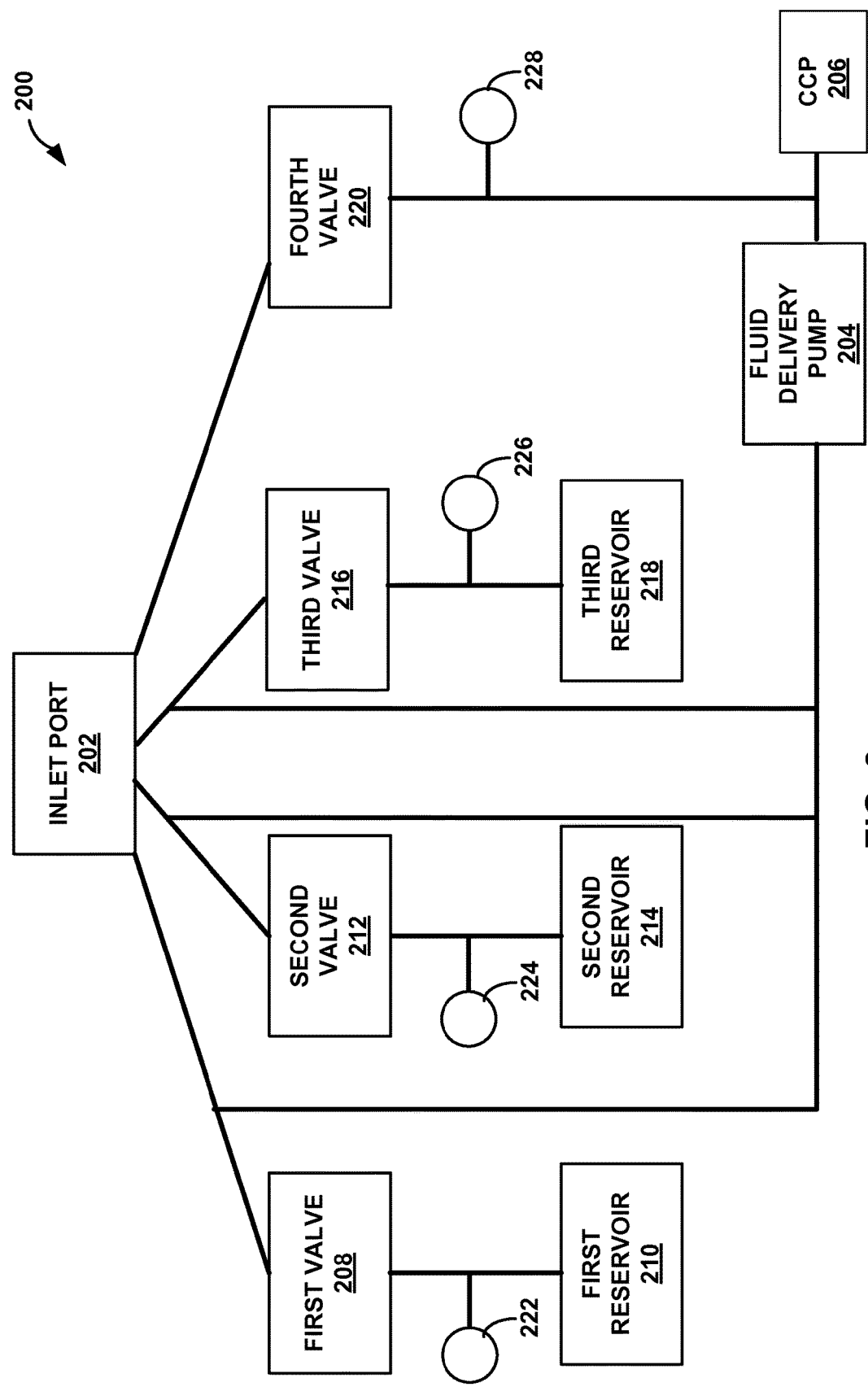
FIG. 8 is a schematic block diagram illustrating fluid communication pathways in an example implantable fluid delivery device.

FIG. 8 is a schematic diagram of a valve scheme for IMD 200, which includes inlet port 202, fluid delivery pump 204, catheter connection port 206, first valve 208, first reservoir 210, second valve 212, second reservoir 214, third valve 216, third reservoir 218, and fourth valve 220. Inlet port 202 is in fluid communication with reservoirs 210, 214, and 218 through valves 208, 212, and 216, respectively. Fluid delivery pump 204 is also in fluid communication with reservoirs 210, 214, and 218 through valves 208, 212, and 216, respectively. IMD 200 provides direct access to catheter connection port 206 from inlet port 202 through fourth valve 220. Sensors 222, 224, 226 and 228 sense a fluid characteristic, e.g., during filling or discharge of reservoirs 210, 214, or 218, respectively, or in the direct catheter access fluid pathway in IMD 200.

The components of IMD 200 may correspond substantially with the components of previously described IMD 12, 100, 400. In some examples, valves 208, 212, 216, and 220, are communicatively connected to at least one processor that controls the opening and closing of valves 208, 212, 216, and 220, e.g., to control the filling of reservoirs 210, 214, or 218 from inlet port 202, or to control fluid withdraw from reservoirs 210, 214, or 218 for delivery through fluid delivery pump 204 to catheter connection port 206. In this manner, IMD 200 allows a single valve to control both flow to a reservoir from inlet port 202 and from a reservoir to fluid delivery pump 204.

When valves 208, 212, 216, and 220 are controlled by a processor in IMD 200, the processor may actuate valves 208, 212, 216, and 220 according to valve sequencing commands. One type of valve sequencing command is a fill command. In a fill command, a user may indicate via an external device communicatively coupled to IMD 200, e.g., programmer 20, an intent to refill a specific fluid, e.g., "drug A" or "first reservoir 210." Programmer 20 transmits instructions, e.g., via telemetry module 88, that cause IMD 200 to open first valve 208 and to close valves 212, 216, and 220. While fluid is delivered or withdrawn through inlet port 202, one or more of sensors 222, 224, 226, and 228 communicate with a processor in IMD 200 and/or programmer 20 to confirm that fluid is being conveyed through first valve 208 but not through valves 212, 216, or 220. A processor in IMD 200 and/or programmer 20 closes first valve 208 after the refill operation, e.g., upon receiving a command from programmer 20 or based on data from sensor 222 indicating that fluid is no longer moving through first valve 208. In various examples, second valve 212, third valve 216, or fourth valve 220 can be actuated to provide fluid access to second reservoir 214, third reservoir 218, or catheter connection port 206, respectively, according to the process outlined for accessing first reservoir 210.

In additional examples, a valve sequencing command for IMD 200 may be a fluid delivery command. In a fluid delivery command, a processor of IMD 200 and/or an external device communicatively coupled to IMD 200, selectively opens and closes valves 208, 212, or 216 while fluid delivery pump 204 is operating to selectively deliver one or more fluid through catheter connection port 206 to patient 16. In some examples, valves 208, 212, and 216 are selectively opened and closed according to specified therapeutic dosing instructions. In some examples, only a single fluid is delivered from either first reservoir 210, second reservoir 214, or third reservoir 218 according to fluid dosing instructions. For example, instructions may specify that 4 microliters per hour of fluid is to be delivered from first reservoir 210 for a period of 6 hours followed by 16 microliters per hour of fluid from second reservoir 214 for a period of 12 hours. Alternatively, dosing instructions may specify delivery of different fluids from different reservoirs 210, 214, 216 substantially simultaneously, e.g., by alternately opening and closing first valve 208, second valve 212, and third valve 216 at a frequency sufficient to allow mixing of the fluid from reservoirs 210, 214, and 218. For example, instructions may specific substantially simultaneous delivery of 8 microliters per hour of fluid from first reservoir 210, 4 microliters per hour of fluid from second reservoir 214, and 15 microliters of fluid from third reservoir 218 through fluid delivery pump 204. In various examples, therapeutic dosing instructions may be stored as part of a therapy program in a memory of IMD 200 or in a memory of an external device communicatively coupled to IMD 200.

Figure 9:
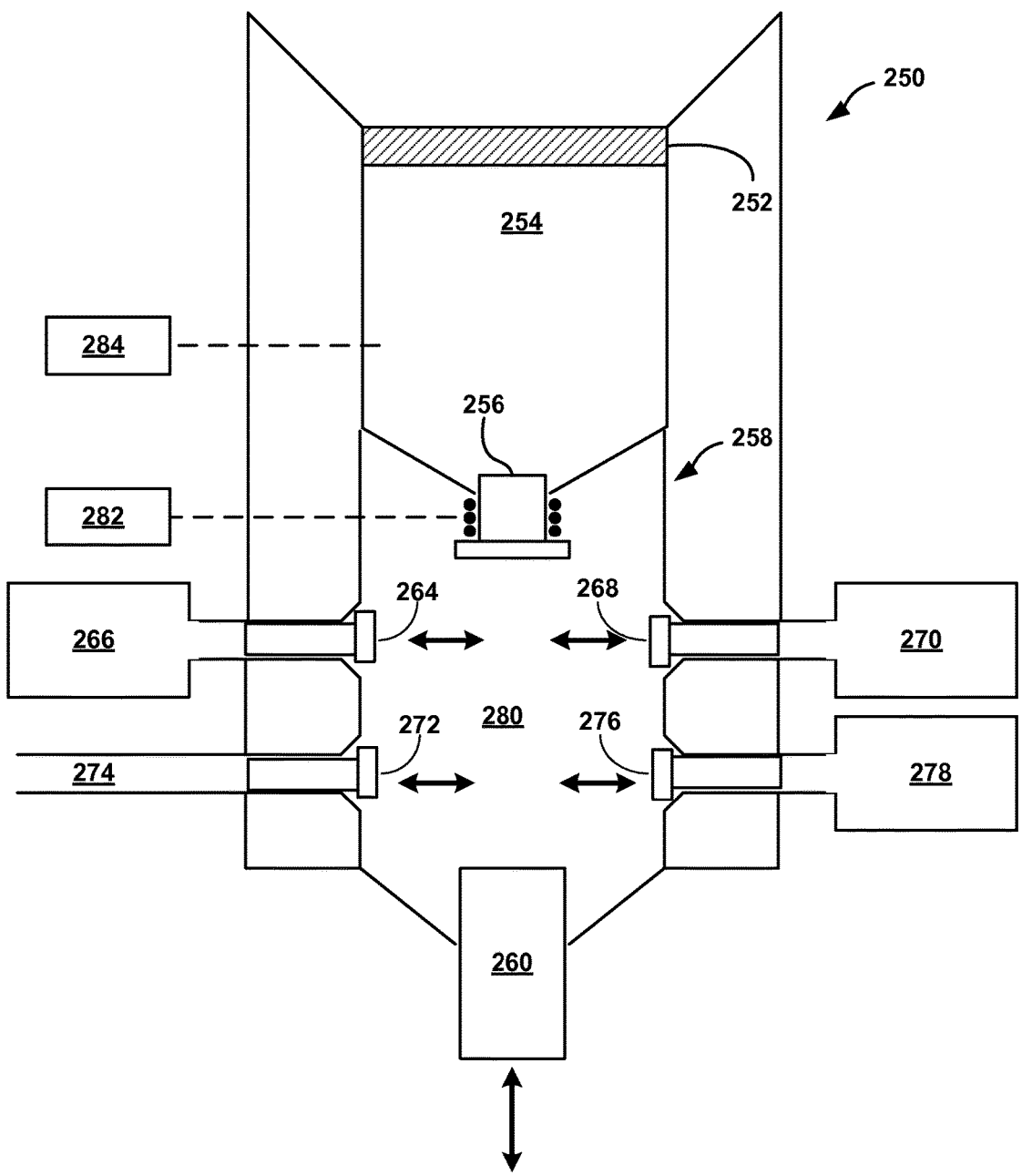
FIG. 9 is a conceptual diagram illustrating an example valve for the example implantable fluid delivery device of FIG. 8.

FIG. 9 is a functional block diagram illustrating components of an example inlet port 250 and valve array 258 that may be used in the valve scheme of FIG. 8. Inlet port 250 defines inlet aperture 254, which is accessible, e.g., using a percutaneous delivery system, through septum 252. Inlet port 250 is configured for fluid communication with valve array 258 through plunger valve 256. Valve array 258 includes first valve 264 controlling fluid pathway access to reservoir 266, second valve 268 controlling fluid pathway access to reservoir 270, third valve 276 controlling fluid pathway access to reservoir 278, and fourth valve 272 controlling fluid pathway access to catheter 274. Fluid delivery pump piston 260 is in fluid connection with fluid chamber 280. Sensor 282 is connected to plunger valve 256. Sensor 284 is connected to refill aperture 254. A processor (not shown) is communicatively coupled to sensors 282 and 284.

In general, valves 264, 268, 272, and 276 are communicatively connected to a processor, e.g., in IMD 12, 100, 200, or 400. Upon receiving instructions from the processor, valve 264, 268, 272, or 276 selectively actuates to open or close fluid pathways. For example, during fluid delivery operation, fluid delivery pump piston 260 moves back and forth in the direction indicated by the arrow in FIG. 9, alternately creating pressure or vacuum in fluid chamber 280. To deliver fluid from first reservoir 266, fluid valve 264 may actuate open during a backstroke of piston 260, resulting in fluid flow from first reservoir 266 to fluid chamber 280 in response to a vacuum generated by the backstroke of piston 260. First valve 264 closes, and piston 260 strokes forward to pressurize the fluid in fluid reservoir 280. Concurrently, fourth valve 272 may actuate open to place fluid chamber 280 in fluid communication with catheter 274, resulting in fluid delivery to patient 16. In various examples, fluid is delivered from second reservoir 270 or third reservoir 278 by a valve actuation scheme analogous to the scheme outlined for delivering fluid from first reservoir 266. Because valve array 258 requires actuation of at least two valves, e.g., first valve 264 and fourth valve 272, during fluid delivery operation, valve array 258 may provide double mechanical redundancy to protect patient 16 from unintended fluid delivery, e.g., valve failure or a stuck valve.

Inlet port 250 and valve array 258 may also provide access for refilling reservoirs 266, 270, 278, or for directly accessing catheter 274. During a therapeutic fluid refill operation, septum 252 may be penetrated, e.g., with a percutaneously inserted fluid delivery needle, to access inlet aperture 254 and plunger valve 256. Plunger valve 256 is biased, e.g., with spring force, to close a fluid pathway between inlet aperture 254 and fluid chamber 280. Plunger valve 256 is configured to be axially depressed to access fluid chamber 280. In some examples, plunger valve 256 is located directly adjacent septum 252 to minimize fluid collection space within inlet aperture 254. A delivery needle depresses plunger valve 256 to access fluid chamber 280. Upon receiving instructions from a processor, at least one of valves 264, 268, 272, or 276 actuates open to open a fluid pathway for delivering fluid from the delivery needle to reservoirs 266, 270, or 278, or catheter 274.

In general, valve array 258 may be separated from inlet port 250 and used in different locations within an IMD, including, e.g., to control fluid delivery from a single fluid pathway to multiple catheters or to control fluid draw from multiple reservoirs to a single fluid delivery pump. In one example, valve array 258 is connected to a sensor including, e.g., sensor 402 in FIG. 5. For instance, reservoir 278 in the example of FIG. 9 may be replaced with a sensor, e.g., sensor 402 in FIG. 5. Valve 264 or 268 is actuated in conjunction with valve 276 to selectively measure a fluid characteristic exhibited by a fluid in either reservoir 266 or 270. Alternatively, valve 264 or 268 is actuated in conjunction with valve 272 to deliver fluid from either reservoir 266 or 270 to catheter 274. As a result, valve array 258 may be used to measure at least one fluid characteristic in two different reservoirs 266, 270, and to control fluid delivery from two different reservoirs 266, 270 to catheter 274.

While valve array 258 in the example of FIG. 9 includes four piston valves 264, 268, 272, 276, in general, any valve that controls the conveyance of fluid through a fluid pathway can be used in the arrangement of FIG. 9 including, e.g., the micro-machined valves described in reference to FIG. 2. In different examples, valve array 258 may include fewer valves or more valves depending, e.g., on the number of fluid pathways in IMD 12, 100, 200, 400.

In various examples, awareness of septum 252 penetration and/or fluid delivery through inlet port 250 may be helpful from the safe and effective operation of IMD 12, 100, 200, 400. Accordingly, in the example of FIG. 9, sensor 282 is in communication with plunger valve 256. Sensor 284 is in communication with inlet aperture 254. Sensors 282, 284 may be used alone, together, or in combination with additional sensors to provide sensory awareness within IMD 12, 100, 200, 400. Sensors 282, 284 may be arranged in a number of locations within IMD 12, 100, 200, 400, including, e.g., in inlet aperture 254, in fluid chamber 280, or in one or more fluid pathways of IMD 12, 100, 200, 400. Regardless where arranged, sensors 282, 284 may be any sensor that detects a fluid characteristic or entry of a percutaneous delivery system into inlet port 250. In one example, sensor 282 detects actuation of plunger valve 256, which may indicate that a delivery needle is axially depressing plunger valve 256. In another example, sensor 284 is a volume flow sensor that detects fluid flow through inlet port 250. In different examples, sensors 282, 284 may be a pressure sensor, volume flow sensor, acoustic sensor, optical sensor, switch-based sensor, inductive sensor, or the like.

In general, sensors 282, 284 communicate with one or more devices including, e.g., programmer 20, to provide an indication of sensed conditions, such as fluid delivery rates through inlet port 250 or that inlet port 250 is being accessed by a delivery system. Upon receiving data related to a condition sensed by sensors 282, 284, the external device may provide a user indication including, e.g., one or more indications described above with reference to programmer 20 in FIG. 3.

Figure 10:
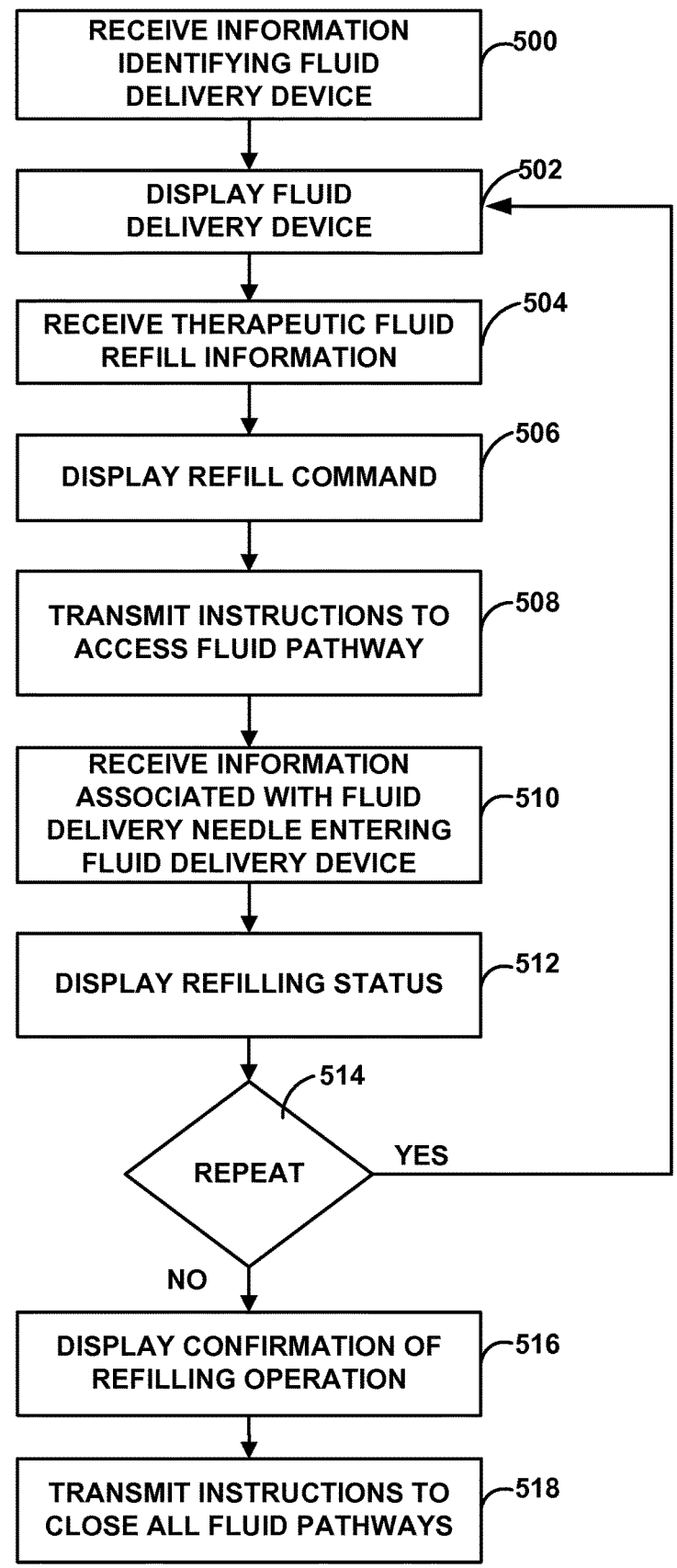
FIG. 10 is a flow chart illustrating an example method for refilling an implantable fluid delivery device.

Different IMD valve configurations and valve actuation procedures have been described in relation to FIGS. 1-9. In different examples, the various valve configurations and valve actuation procedures can be incorporated into therapeutic fluid refilling procedures. FIG. 10 is a flow chart illustrating an example method for refilling a fluid reservoir in an IMD through an inlet port in fluid communication with a controllable valve. In particular, FIG. 10 illustrates an example method for refilling a fluid reservoir in an IMD that houses multiple reservoirs, where each reservoir includes a fluid pathway extending between the reservoir and a controllable valve which in turn is in fluid communication with an inlet port. The method of FIG. 10 includes receiving information identifying a fluid delivery device to be accessed (500), displaying a fluid delivery device (502), and receiving therapeutic fluid refill information (504). The method of FIG. 10 also includes displaying a refill command (506), transmitting instructions to access a fluid pathway (508), receiving information associated with a fluid delivery needle entering the fluid delivery device (510), and displaying refilling status (512). In some examples, the method of FIG. 10 is repeated to fill a different reservoir in fluid delivery device (514). After suitably filling one or more reservoirs in the fluid delivery device, the method of FIG. 10 includes displaying confirmation of the refilling operation (516) and transmitting instructions to close all fluid pathways (518).

For ease of description, the functions of the method of FIG. 10 for refilling a fluid reservoir in an IMD with multiple fluid reservoirs are described as executed by programmer 20 (FIG. 3) and IMD 100 (FIG. 4), and in particular memory 86 and processor 84 of programmer 20 and memory 104 and processor 102 of IMD 100. In other examples, however, the method of FIG. 10 may be executed in IMD 12, 200, 400, or IMDs with different configurations, as described herein. In addition, in other examples, one or more functions may be carried out solely by IMD 100, solely by programmer 20, or solely by another device communicatively coupled to IMD 100. Alternatively, one or more functions associated with the method of FIG. 10 may be carried out by several devices working cooperatively.

At various times, different patients with different types of implantable medical devices may pass through a clinical setting to receive medical service and treatment. In some cases, a patient is able to receive medical service and treatment at home, whether self-administered or administered by a third party. In either case, some patients have multiple IMDs, e.g., to deliver different types of therapies or to deliver therapy to different target locations. As a result, a user may need to locate and identify IMD 100 before proceeding with a reservoir refilling procedure.

The method of FIG. 10 includes receiving information identifying IMD 100 that includes first reservoir 112 and second reservoir 114 (500). In one example, a user directly enters information that identifies IMD 100, e.g., a patient name, a unique identification number associated with either the patient or IMD 100, or the like, into user interface 82 of programmer 20. In response to the entered information, processor 84 of programmer 20 pulls stored patient information, e.g., patient history or the hardware configuration of IMD 100, from memory 86 for display on user interface 82. In another example, a user enters a command in user interface 82 of programmer 20 to locate all fluid delivery devices within the communication range of programmer 20. Processor 84 transmits a query through telemetry module 108 for all fluid delivery devices within the communication range of programmer 20 to respond. IMD 100 receives the query command and processor 102 of IMD 100 transmits a response including, e.g., a unique identification number associated with IMD 100, a unique identification number associated with patient 16 in which IMD 100 is implanted, and/or information identifying the hardware configuration of IMD 100. In some examples, processor 84 of programmer 20 controls user interface 82 to display a list of different patients, or a list of different IMDs within a specific patient, based on responses from a plurality of different IMDs within the communication range of programmer 20. In these examples, a user may be able to select via programmer 20 a specific patient or a specific IMD 100 from the presented list for further attention.

In some examples, the user selects the specific patient via programmer 20, and IMD 100 is the only device implanted within the patient. However, many patients have multiple IMDs, and further device identification may be necessary to distinguish IMD 100 from different devices implanted within the patient. Accordingly, in some examples, processor 84 of programmer 20 may control user interface 82 to display an indication, e.g., graphical, of the different IMDs within the patient and/or the relative location of the different IMDs within the body of the patient. Programmer 20 may generate the display based, e.g., on the unique identification number associated with patient 16 and/or the unique identification number associated with IMD 100, based on information associated with the patient that is stored in memory 86 of programmer 20 or memory 104 of IMD 100. In some examples, the user may crosscheck the indication provided by programmer 20 with, e.g., paper or other electronic records, to confirm that the IMDs identified by programmer 20 are correct for the specific patient. In some examples, programmer 20 may display a command prompt requesting the user to select one or more fluid delivery devices to refill.

In some examples, a user can limit the number of IMDs responding to commands received from programmer 20, thereby reducing or eliminating the size of a selection list used for selecting IMD 100 to refill. In one example, programmer 20 may transmit instructions specific to an IMD or group of IMDs, including IMD 100. In another example, a user may selectively initiate communication with IMD 100. Using programmer 20 or another device communicatively coupled to IMD 100, IMD 100 may receive information identifying programmer 20 and indicating that programmer 20 is seeking to establish communication with IMD 100. For example, programmer 20 may be communicatively coupled to a telemetry module configured to communicate using RF or near field communication techniques. The telemetry module may be physically positioned over IMD 100, allowing IMD 100 receive wakeup instructions, unique identification information for programmer 20, and/or any additional supporting information for programmer 20 from the telemetry module. After initiating a communication session, IMD 100 may communicate with programmer 20.

Having identified IMD 100 for further attention, the method of FIG. 10 may include displaying IMD 100 (502). In different examples, processor 84 of programmer 20 may control user interface 82 to provide a textual or graphic indication of the hardware configuration of IMD 100. In some examples, programmer 20 is configured to display graphical pictures, sketches, or other images representative of: inlet port 116, first valve 122, second valve 124, first reservoir 112, second reservoir 114, fluid delivery pump 110, various fluid pathways, and/or other features of IMD 100. In some examples, programmer 20 is configured to provide a textual indication of the hardware configuration of IMD 100.

The method of FIG. 10 includes receiving therapeutic fluid refill information (504). With appropriate knowledge of the hardware configuration of IMD 100, a user may select, and programmer 20 may receive, information identifying one or more reservoirs of IMD 100 to be refilled. Programmer 20 may receive additional or different information about a planned refilling operation. For example, programmer 20 may receive information related to the number of reservoirs of IMD 100 to be refilled or the amount of fluid to be added or withdrawn from each reservoir of IMD 100. In additional examples, programmer 20 may receive information assigning a specific therapeutic fluid to first reservoir 112 and/or second reservoir 114. By assigning a specific therapeutic fluid to a reservoir, a user may designate a therapeutic fluid to be refilled and housed in a specific reservoir. For example, a user may indicate that different fluids, e.g., morphine and baclofin, are assigned to reservoir 112 and reservoir 114, respectively. Alternatively, a user may designate one of reservoirs 112, 114 as an empty reservoir, indicating that fluid will not be discharged into the empty reservoir. The assignments may be stored in memory 104 of IMD 100 or memory of another device communicatively coupled to IMD 100.

With refill information entered, programmer 20 may display a graphical indication of the configuration of IMD 100 and the fluids assigned to first reservoir 112 and/or second reservoir 114. In some examples, processor 84 may control user interface 82 to display a command prompt requesting that the user confirm that user interface 82 accurately reflects the hardware configuration of IMD 100 and/or the refill information entered by the user. In some examples, programmer 20 may receive updated refill information, e.g., changed therapeutic fluid assignment information, if user interface 82 does not display the refill information the user intended.

The method of FIG. 10 may include displaying a refill command prompt (506). After receiving refill information (504), programmer 20 may provide one or more command prompts to guide a user through a refilling operation. In some examples, processor 84 controls user interface 82 to provide a command to prompt a user to fill a fluid delivery system, e.g., a hypodermic needle and syringe, with a therapeutic fluid previously assigned via programmer 20. In one example, programmer 20 displays a command prompt asking the user to indicate via user interface 82 that the fluid delivery system has been filled with the assigned therapeutic fluid. In another example, the fluid delivery system may come prefilled with the assigned therapeutic fluid. In some examples, programmer 20 displays a command prompt asking the user to enter a bar code from the prefilled fluid delivery system. In this manner, programmer 20 can cross-reference the contents of the actual therapeutic fluid with the assigned therapeutic fluid to confirm the integrity of the refilling operation. If the actual therapeutic fluid does not match the assigned therapeutic fluid, programmer 20 may, e.g., provide a warning to user interface 82 and terminate the refilling operation.

Upon receiving acknowledgment from a user that the user is ready to proceed with the refilling operation, processor 84 of programmer 20 may control telemetry module 88 to transmit an instruction to open fluid pathway 121 or 123 in IMD 100 (508). Processor 102 in IMD 100 receives the instruction and transmits a command to actuate either first valve 122 or second valve 124 to an open position, thereby opening either fluid pathway 121 to first reservoir 112 or fluid pathway 123 to second reservoir 114. In some examples, processor 102 of IMD 100 transmits a confirmation message back to programmer 20 indicating that either first valve 122 or second valve 124 was actuated open. Upon receiving the message from IMD 100, programmer 20, in some examples, displays a indication, e.g., graphical or textual, of IMD 100 that identifies either first valve 122 and fluid pathway 121 or second valve 124 and fluid pathway 123 as open, while the corresponding valve and fluid pathway are identified as closed.

With a fluid pathway opened in IMD 100, a user may insert a fluid delivery needle into inlet port 116 of IMD 100. In one example, programmer 20 displays a command prompt instructing a user to insert the fluid delivery needle into inlet port 116 through septum 120. In another example, the user proceeds without a command prompt from programmer 20. The user may identify inlet port 116, or distinguish inlet port 116 from other inlet ports, based on a variety of techniques including, e.g., tactile feel, with the aid of an inlet port identification template place over the patient's skin, or with the aid of an electronic port finding device (EPF) that helps the user find an inlet port and/or distinguish different inlet ports.

Inlet port identification may be easy with a patient that has a single IMD with a single inlet port. In other examples, however, a patient may have multiple implanted devices and/or an IMD with multiple inlet ports. To protect against accessing the wrong inlet port, programmer 20 may be configured to transmit a signal to all IMDs within the communication range of programmer 20 to enable a sensor in each IMD to detect needle entry into an inlet port. For example, a sensor configured to detect entry into an inlet port may include, e.g., plunger valve 256 described in relation to FIG. 9. In some examples, programmer 20 transmits a signal to IMD 100 (i.e., the fluid delivery device to be accessed) informing IMD 100 that the device should expect entry into inlet port 116. Programmer 20 may also inform IMD 100 that the device should not expect entry into a different inlet port, such as an inlet port in fluid communication with a direct catheter access fluid pathway. Programmer 20 may also transmit a signal to other devices implanted within patient 16 indicating that the devices should not expect entry into an inlet port.

Regardless of how a user identifies inlet port 116, the method of FIG. 10 may include receiving information associated with a fluid delivery needle entering inlet port 116 of IMD 100 (510). In one example, IMD 100 includes a sensor that detects entry into inlet port 116, e.g., plunger valve 256 described in relation to FIG. 9. Processor 102 of IMD 100 may analyze the sensor data, determine that a fluid delivery needle entered inlet port 116, and transmit an indication to programmer 20, e.g., to be displayed via user interface 82. Alternatively, sensor data may be streamed through telemetry module 108 of IMD 100 to processor 84 of programmer 20, allowing processor 84 to analyze and determine that a fluid delivery needle entered inlet port 116.

In some examples, if the user accesses the wrong port of IMD 100, e.g., an inlet port in fluid communication with a direct catheter access fluid pathway, or an inlet port on a different implanted device other than IMD 100, the accessed device may transmit a message to programmer 20. In turn, programmer 20 may issue a message to the user via user interface 82 indicating the unexpected inlet port access. In some examples, the accessed device may itself issue an alarm from within the patient upon detecting entry into an inlet port. The alarm may include, e.g., an audible alarm, vibration, or the like.

To further protect against entering the wrong inlet port, implanted devices that include a controllable valve adjacent to an inlet port, such as valves 122, 124 in IMD 100, may close the valve to block fluid discharge into the device. That is, in response to receiving instructions from programmer 20 that an implanted device is not to be refilled, the implanted device may actuate all inlet port valves closed to block access to the inlet port. In an additional example, IMD 100, which is accessed during a refill operation through inlet port 116, may actuate inlet valves that are not adjacent to inlet port 116 closed including, e.g., a valve adjacent an inlet port in fluid communication with a direct catheter access fluid pathway. In this manner, implanted devices may provide a mechanical barrier to protect against inadvertent access to a wrong inlet port.

The method of FIG. 10 may also include displaying refill status information via user interface 82 of programmer 20 (512). Sensors in IMD 100 may detect fluid flow from a fluid delivery needle into IMD 100 during the refill operation. In one example, IMD 100 includes a sensor, e.g., a volume sensor or pressure sensor, in a reservoir being refilled. Accordingly, processor 102 of IMD 100 may analyze the sensor data and determine a filling characteristic including, e.g., an absolute volume of fluid in the reservoir being filled or a fill percentage. IMD 100 may transmit the determined filling characteristic via telemetry modules 108 and 88 to programmer 20, e.g., to be displayed via user interface 82, thereby allowing a user to track reservoir filling progress. Alternatively, sensor data may be streamed through telemetry module 108 of IMD 100 to processor 84 of programmer 20, allowing processor 84 to analyze and determine a reservoir filling characteristic to track reservoir filling progress. In any event, programmer 20 may display the determined reservoir filling characteristic. In some examples, user interface 82 of programmer 20 displays an indication, e.g., graphical, of IMD 100 that illustrates therapeutic fluid flowing into the assigned reservoir on a real-time basis. Further, although the method of FIG. 10 is described as discharging fluid into IMD 100 and/or sensing during the discharge process, in additional examples, fluid may be extracted from IMD 100 and/or sensed during the extraction process.

Refill status information may also include information related to the termination of a refill operation. A user may stop a refilling operation for various reasons. In one example, a user may stop a refill operation after delivering all (or a desired amount) of the fluid provided in a fluid delivery syringe into IMD 100. Accordingly, programmer 20 may display an indication via user interface 82, e.g., based on reservoir filling progress, indicating that a select reservoir is full and that the user should stop refilling. Alternatively, programmer 20 may provide an indication that a select reservoir has reached a target filling point, e.g., established by the user at the beginning of the refilling operation. In another example, the user may prematurely terminate the reservoir filling process, e.g., by accidentally withdrawing the fluid delivery needle from inlet port 116. To ensure that the user is aware of the fluid refilling process, programmer 20, in various examples, may issue an alert via user interface 82 when a select fluid reservoir is not filled as programmer 20 otherwise expects based on stored instructions. For example, programmer 20 may provide an alert if a user did not fill a reservoir to capacity or if a user discharged more or less fluid into the reservoir than the user originally targeted. In any case, the user may stop a refilling operation at an appropriate time.

After suitably filling a first selected reservoir, first valve 122 or second valve 124 may be actuated closed to close the fluid pathways connecting inlet port 116 to reservoirs 112, 114. In some examples, first valve 122 or second valve 124 is closed after programmer 20 transmits, and IMD 100 receives, instructions indicating that refilling is terminated and that the appropriate valve should actuate close. In some examples, processor 102 of IMD 100 automatically closes either first valve 122 or second valve 124, e.g., based on sensor data indicating that refilling has terminated.

In general, the method outlined above for filling a first selected reservoir may be repeated to fill a different reservoir 112, 114 in IMD 100 (514). In one example, programmer 20 displays a refill command (506) via user interface 82, instructing the user to reinitiate the refilling sequence outline above with respect to a first selected reservoir for a different reservoir in IMD 100. In this manner, the refilling process may be repeated until, e.g., all the reservoirs in IMD 100 are filled. In some examples, programmer 20 displays a continuously updating visual indication of the refilling process on user interface 82, e.g., first indicating that all reservoirs empty, then indicating valve actuation and fluid flow into a first selected reservoir, then indicating the first reservoir is full, then indicating further valve actuation and fluid flow into a second selected reservoir, indicating the second reservoir is full, and the like. In some examples, at the end of the refilling operation, programmer 20 displays a confirmation message (516) via user interface 82 indicating that that all reservoirs were properly filled, e.g., according to refill information received at the beginning of the refill operation (504). In one example, programmer 20 displays a visual illustration of each reservoir before, during, and/or after the refilling process, e.g., illustrating each reservoir as full, empty, or partially filled.

The method of FIG. 10 also includes transmitting instructions to close fluid pathways 121, 123 (518). At the end of the reservoir refilling operation process, valves 122 and 124 may both actuate closed to close fluid communication between inlet port 116 and reservoirs 112, 114. In one example, programmer 20 transmits instructions to IMD 100, e.g., upon user input indicating that the refilling process is terminated or after a programmed refill process is completed, to close valves 122 and 124. In another example, processor 102 of IMD 100 automatically closes valves 122 and 124, e.g., based on sensor data indicating that refilling has terminated. In either case, closed valves 122 and 124 provide a mechanical barrier between inlet port 116 and reservoirs 112, 114 during subsequent operation of IMD 100. The mechanical barrier may prevent unintended fluid exchange between inlet port 116 and reservoirs 112, 114. The mechanical barrier may also prevent inadvertent access to inlet port 116, e.g., access when a user is attempting to enter a different inlet port on IMD 100 or a different device entirely.

Periodically, a user may deviate from the refilling process outlined above based, e.g., on a desire to change fluid assignments (i.e., to change a specific fluid assigned to a specific reservoir) or on user time constraints. Accordingly, programmer 20, in some examples, may be configured to allow the user to alter a planned refilling operation. In one example, programmer 20 is configured to allow the user to abort the refilling procedure after the procedure is initiated. Programmer 20 may automatically transmit instructions to close valves 122 and 124 upon receiving a user abort command. In another example, programmer 20 is configured to allow the user to change fluid assignments after the refilling procedure begins. This configuration may be beneficial if the user realizes, e.g., that the wrong fluid is being injected into the wrong reservoir and thus the user needs to change reservoir assignments. In some examples, programmer 20 may be configured to provide a user with command prompts and task flow options to facilitate making changes to a fluid refill procedure, e.g., instructing the user how to restart the refilling procedure, change fluid assignments, transmit instructions to actuate one or more valves, open or close various fluid pathways, or the like. In one example, upon receiving instructions indicating that a user wants to make a change to a refill operation after starting the refill process, programmer 20 is configured to display step-by-step instructions via user interface 82 to guide the user in making the change. Instructions may include, e.g., requesting whether the user wants to remove and/or replace fluid in first reservoir 112 after first reservoir 112 has been filled, requesting whether the user wants to swap a fluid filled in first reservoir 112 with a fluid filled in second reservoir 114, e.g., by reassigning the different fluids, requesting whether the user wants to increase or reduce the amount of fluid in first reservoir 112 after finishing the refill operation with respect to first reservoir 112, or the like.

During the refilling method of FIG. 10, IMD 100 and programmer 20, either alone or in combination, may capture and store various event history information. In one example, IMD 100 and/or programmer 20 captures and stores time stamps identifying when a refill operation began and/or ended for each reservoir in IMD 100. In another example, IMD 100 and/or programmer 20 captures and stores the fluid assigned to each reservoir by the user at the beginning of the refill operation. That is, IMD 100 and/or programmer 20 may capture and store the fluid that the user intended to deliver to each reservoir. In another example, IMD 100 and/or programmer 20 may capture and store the volume of fluid delivered to each reservoir during the refill operation and/or the volume of fluid the user intended to deliver to each reservoir, as indicated at the beginning of the refill operation. In an additional example, IMD 100 and/or programmer 20 may capture and store information identifying whether more or less fluid was delivered to a selected reservoir than the user intended to deliver, as indicated at the beginning of the refill operation. In another example, IMD 100 and programmer 20 may capture and store information identifying whether fluid was refilled to all reservoirs as planned or if a refill operation was in any way aborted or modified after the refill operation was initiated.

In different examples, event history information can be processed and stored by IMD 100, programmer 20, and/or another external device communicatively coupled to IMD 100. In one example, processor 102 of IMD 100 logs event history information, obtains additional event history information from programmer 20 through telemetry modules 88 and 108, as needed, and stores the event history information in memory 104 of IMD 100. In another example, processor 84 logs event history information, obtains additional event history information from IMD 100 through telemetry modules, as needed, and transmits the event history information to IMD 100 for storage in memory 104 of IMD 100. In some examples, processor 84 logs event history information, obtains additional event history information from IMD 100 through telemetry modules, as needed, and stores the event history information in memory 86 of programmer 20. In one example, processor 84 logs event history information, obtains additional event history information from IMD 100 through telemetry modules, as needed, and stores the event history information in both memory 104 of IMD 100 and memory 86 of programmer 20. In general, event history information may be any information related to accessing IMD 100 or performing a therapeutic fluid refilling operation.

As noted, event history information can be stored by IMD 100, programmer 20, and/or another external device communicatively coupled to IMD 100. In some examples, event history information is stored in an electronic medical record (EMR) associated with a specific patient. In some examples, event history information is stored on a remote server in addition to, or in lieu of, being stored on IMD 100 or programmer 20. Programmer 20 or another device communicatively coupled to IMD 100 may transmit event history information using a secure or an unsecure connection. A connection for transmitting event history information may include, but is not limited to, a public switched telephone network (PSTN), a cellular communication network, a radio communication network, the Internet, or some other communication network.

Although the method of FIG. 10 outlined above describes a process for refilling a fluid reservoir in an IMD with multiple fluid reservoirs, in other examples, the method of FIG. 10 may be executed with an IMD that includes a different hardware configuration. In one example, the method of FIG. 10 can be executed with IMD 12 that includes catheter access fluid pathway 40. In this example, a user can employ programmer 20, in conjunction with, or in lieu of, another device communicatively coupled to IMD 12, to identify inlet port 42 and actuate valve 36, thereby providing direct access to catheter 18 according to the method outlined in FIG. 10.

In another example, the method of FIG. 10 can be used to refill an IMD with a single fluid reservoir in addition to, or in lieu of, refilling a multi-reservoir IMD. That is, the method of FIG. 10 can be used to refill a fluid reservoir in an IMD even if the IMD does not include a controllable valve or multiple fluid reservoirs. In particular, in examples where a patient includes multiple implanted fluid delivery devices, the method of FIG. 10 can be used to safely identify and refill a specific IMD that is targeted from a plurality of IMDs implanted within the patient. To illustrate, the method of FIG. 10 is described below for refilling a single reservoir IMD selected from a plurality of IMDs implanted in a patient. In general, the various hardware components and operation of a single reservoir IMD may correspond to the hardware and operational descriptions provided herein. Further, although aspects of the example implementation of the method of FIG. 10 are summarized below for brevity, it should be appreciated that any and all details described above with respect to refilling a multi-reservoir IMD can be used in refilling a single reservoir IMD that selected from a plurality of implanted IMDs.

Following the method of FIG. 10, programmer 20 may receive information identifying a fluid delivery device to be accessed. A user may identify a specific IMD to be refilled including, e.g., a single-reservoir IMD selected from a plurality of IMDs implanted in a patient. In various examples, the user directly enters information into programmer 20 that identifies either the patient or the specific IMD to be refilled, as described above. Alternatively, the user enters a command into programmer 20 to locate all fluid delivery devices within the communication range of programmer 20, which is also described above. In either example, programmer 20 may display via user interface 82 an indication, e.g., graphical, of the different IMDs within the patient and/or the relative location of the different IMDs within the body of the patient. In general, programmer 20 may receive information from a user selecting a specific IMD to be refilled from the plurality of IMDs implanted in a patient. In alternative examples, selective communication may be established between programmer 20 and a specific IMD, e.g., using a telemetry module physically positioned over the specific IMD, as described above. In this manner, a user may select a specific IMD for further attention without selecting the IMD from a listing of different IMDs.

In some examples, the user selects a plurality of IMDs to be refilled, e.g., sequentially as part of a clinician visit. In any event, a refilling procedure may include receiving therapeutic fluid refill information. A user may assign a therapeutic fluid to a specific IMD to be refilled, e.g., through user interface 82. Where the user selected a plurality of IMDs to be refilled, the user may sequentially assign a therapeutic fluid to the reservoir of each IMD to be refilled. The therapeutic fluid assignments may be stored in a memory of each IMD to be refilled, memory 104 of programmer 20, or another memory. With therapeutic fluid assignments completed, programmer 20, in some examples, may display a graphical indication of the configuration of the IMD or IMDs to be refilled and the fluid assigned to the IMD or IMDs to be refilled. In some examples, programmer 20 displays a query requesting that the user confirm that user interface 82 accurately reflects the IMD or IMDs to be refilled and the fluid selections entered by the user for each IMD.

Upon receiving confirmation that the user agrees with the IMD selection and fluid assignment(s), programmer 20 may display a refill command prompt instructing the user to fill a fluid delivery needle with a therapeutic fluid previously assigned via programmer 20, e.g., a therapeutic fluid assigned to a specific IMD. Alternatively, the user may indicate via programmer 20 a specific fluid the user desires to refill, and programmer 20 may automatically select the IMD to be refilled based on previously established therapeutic fluid assignments. Where two or more IMDs are assigned the same fluid, programmer 20 may be configured to receive a user selection in which the user selects an IMD to be initially refilled from the two or more IMDs assigned the same fluid. In various examples, programmer 20 may be configured to receive a user input indicating that the user is ready to continue with the refilling operation.

Upon indicating that the user is ready to refill a selected IMD, programmer 20 may transmit a signal to the IMD to be refilled, or all IMDs within the communication range of programmer 20, to enable a sensor configured to detect entry of a needle into an inlet port. In one example, a sensor configured to detect entry of a needle into an inlet port in fluid communication with a reservoir is enabled. In another example, a sensor configured to detect entry of a needle into an inlet port in fluid communication with a direct catheter access fluid pathway is enabled. In an additional example, both a sensor configured to detect entry of a needle into an inlet port in fluid communication with a reservoir and a sensor configured to detect entry of a needle into an inlet port in fluid communication with a direct catheter access fluid pathway is enabled. As described above, in some examples, programmer 20 transmits instructions to the specific IMD to be refilled informing the IMD that the device should expect entry into an inlet port. In some examples, programmer 20 may inform other IMDs implanted in the patient that the devices should not expect entry into an inlet port. As a result, an alarm may be issued if an IMD not selected for immediate refill detects a fluid delivery needle in an inlet port. In various examples, programmer 20 displays a message user via user interface 82 indicating unexpected inlet port access. In some examples, the accessed device may itself issue an alarm from within the patient upon detecting entry into an inlet port, as described above.

Further, to protect against unintentional access, a single reservoir IMD may include a controllable valve located adjacent an inlet port, as described herein. The controllable valve may actuate closed in each IMD not being refilled. In addition, in some examples, a controllable valve in an IMD to be refilled may require actuation to open before a refilling process can proceed.

Regardless of the specific hardware configuration, programmer 20 may receive information associated with a fluid delivery needle entering a specific IMD, e.g., according to the techniques described above. In some examples, programmer 20 provides an indication, e.g., audible, visual, or tactile, when a fluid delivery needle is inserted into a correct inlet port. In additional examples, programmer 20 may provide a different indication, e.g., different audible, different visual, or different sensation such as tactile versus audible, when the fluid delivery needle is unexpectedly inserted into an inlet port of an IMD not selected for immediate refill. According to one example, programmer 20 may display a command prompt instructing a user to refill a specific IMD if a fluid delivery needle is detected in the correct inlet port.

In general, a sensor in the IMD being refilled may be used to detect fluid flow from the fluid delivery needle into the IMD, as described above. In various examples, user interface 82 of programmer 20 may display an indication, e.g., graphical, of the IMD being refilled that illustrates therapeutic fluid flowing into the reservoir of the IMD on a real-time basis.

Similar to the process for refilling an IMD with multiple reservoirs, programmer 20 may display an indication via user interface 82, e.g., based on reservoir filling progress, indicating that the reservoir of the specific IMD to be filled is full or has reached a target filling point previously indicated by the user, and, as a result, the user should stop the discharging fluid into the IMD. In some examples, programmer 20 provides an alert to user interface 82 when the reservoir is not filled as programmer 20 otherwise expects, e.g., based on stored instructions. For example, programmer 20 may provide an alert if: a needle is unexpectedly withdrawn from the inlet port of the IMD being refilled, the user did not fill the reservoir to capacity, or if the user discharged more or less fluid into the reservoir than the user originally targeted.

Regardless, after suitably filling the reservoir of the first selected IMD, the method outlined above may be repeated to fill additional IMDs including, e.g., IMDs previously selected for refilling and assigned therapeutic fluid. Throughout the refilling process, programmer 20 may display a continuously updating visual indication of the refilling process on user interface 82, e.g., indicating a first IMD and reservoir to be refilled, then indicating fluid flow into the first selected IMD, then indicating that the reservoir of the first selected IMD is full, then indicating a second IMD and reservoir to be refilled, and the like. In some examples, programmer 20 may display confirmation of a refilling operation indicating that all selected IMDs were properly filled, e.g., according to an information received at the beginning of the refill operation.

In one example, programmer 20 displays a visual illustration of each IMD before, during, and/or after the refilling process, e.g., illustrating a reservoir of each IMD as full, empty, or partially filled. In addition, is some examples, one or more of the IMD being refilled and/or programmer 20, either alone or in combination, may capture and store various event history information, as described above. Thus, according to the foregoing, the method of FIG. 10 can be used to refill a specific IMD that is selected from a plurality of IMDs implanted within a patient.

While in the preceding examples a target therapy delivery site(s) was described as being proximate to the spinal cord of a patient, other applications of therapy systems in accordance with this disclosure include alternative delivery sites. In some examples, a target therapy delivery site may be in one or more limbs of a patient. In some examples, the target delivery site may be proximate to different types of tissues including, e.g., nerves, e.g. sacral, pudendal or perineal nerves, organs, muscles or muscle groups. In one example, a catheter may be positioned to deliver a therapeutic fluid to a deep brain site or within the heart or blood vessels. Delivery of a therapeutic fluid within the brain may help manage a number of disorders or diseases including, e.g., chronic pain, diabetes, depression or other mood disorders, dementia, obsessive-compulsive disorder, migraines, obesity, Alzheimer's disease, auto-immune conditions, and movement disorders, such as Parkinson's disease, spasticity, and epilepsy. A catheter may also be positioned to deliver insulin to a patient with diabetes. In other examples, the system may deliver a therapeutic fluid to various sites within a patient to facilitate other therapies and to manage other conditions including peripheral neuropathy or post-operative pain mitigation, ilioinguinal nerve therapy, intercostal nerve therapy, gastric drug induced stimulation for the treatment of gastric motility disorders and/or obesity, and muscle stimulation, or for mitigation of peripheral and localized pain e.g., leg pain or back pain.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. An implantable therapeutic fluid delivery system comprising:
a first fluid pathway configured to convey a first therapeutic fluid;
a second fluid pathway configured to convey a second therapeutic fluid, the second fluid pathway being separate from the first fluid pathway;
a valve connected to the first fluid pathway and the second fluid pathway;
a pump, the first fluid pathway being fluidly connected to the pump;
a reservoir, the first fluid pathway being fluidly connected to the reservoir;
an inlet port configured to receive the first therapeutic fluid and the second therapeutic fluid, wherein the valve is interposed between the inlet port and the reservoir along the first fluid flow pathway;
a processor configured to actuate the valve to selectively open and close the first fluid pathway to control access to the reservoir, and to selectively open and close the second fluid pathway;
a housing configured to be implanted in a patient, wherein the first fluid pathway, the second fluid pathway, the valve, and the reservoir are housed within the housing; and
a catheter connection port configured to connect to a catheter;
wherein the first fluid pathway extends from the inlet port to the catheter connection port and is fluidly connected to the catheter connection port, and the reservoir is interposed between the valve and the catheter connection port along the first fluid pathway, and
wherein the second fluid pathway extends from the inlet port to the catheter connection port and is directly fluidly connected to the catheter connection port without passing through any reservoir or any pump, and the valve is interposed between the inlet port and the catheter connection port along the second fluid pathway;
wherein the system is configured to deliver:

the first therapeutic fluid, via the first fluid pathway, from the inlet port, through the valve, through the reservoir, through the pump, and out the catheter connection port; and
the second therapeutic fluid, via the second fluid pathway, from the inlet port, through the valve, and out the catheter connection port.

2. The implantable therapeutic fluid delivery system of claim 1, wherein the valve comprises a rotary valve.

3. The implantable therapeutic fluid delivery system of claim 1, wherein the valve comprises a first valve connected to the first fluid pathway and a second valve connected to the second fluid pathway, wherein the processor is configured to control actuation of the first valve to open and close the first fluid pathway and to control actuation of the second valve to open and close the second fluid pathway.

4. The implantable therapeutic fluid delivery system of claim 1, wherein the inlet port is located on a peripheral surface of the housing.

5. The implantable therapeutic fluid delivery system of claim 4, wherein the valve comprises a first valve connected to the first fluid pathway and a second valve connected to the second fluid pathway, and wherein the processor is configured to control actuation of the first valve to open and close the first fluid pathway and to control actuation of the second valve to open and close the second fluid pathway.

6. The implantable therapeutic fluid delivery system of claim 4, further comprising a sensor configured to detect entry of a needle into an aperture defined by the inlet port.

7. The implantable therapeutic fluid delivery system of claim 6, wherein the sensor comprises at least one of a flow sensor, plunger valve, pressure sensor, acoustic sensor, optical sensor, switch-based sensor, and inductive sensor.

8. The implantable therapeutic fluid delivery system of claim 6, wherein the processor is configured to control actuation of the valve based at least upon a signal provided by the sensor.

9. The implantable therapeutic fluid delivery system of claim 6, further comprising a memory configured to store an indication when the sensor detects entry of the needle.

10. The implantable therapeutic fluid delivery system of claim 4, further comprising a programmer configured to receive user input, wherein the processor is configured to control actuation of the valve based at least upon the user input.

11. The implantable therapeutic fluid delivery system of claim 10, wherein the processor is configured to cause the programmer to display a fluid pathway indication when at least one of the first fluid pathway or second fluid pathway is open.

12. The implantable therapeutic fluid delivery system of claim 11, wherein the programmer comprises the processor.

13. The implantable therapeutic fluid delivery system of claim 10, further comprising a sensor configured to detect entry of a needle into an aperture defined by the inlet port, wherein the processor is configured to control actuation of the valve based at least upon the user input and a signal provided by the sensor.

14. The implantable therapeutic fluid delivery system of claim 13, wherein the processor is configured to control actuation of the valve to close the first and second fluid pathways if the sensor detects entry of the needle into the aperture defined by the inlet port and the user input did not indicate that the needle would be entering the aperture defined by the inlet port.

15. The implantable therapeutic fluid delivery system of claim 14, wherein the processor is configured to at least one of cause the programmer to display an indication that the sensor detected entry of the needle into the aperture, issue an audible, visual, or tactile alarm, or store an indication that the sensor detected entry of the needle into the aperture in a memory.

16. The implantable therapeutic fluid delivery system of claim 4, wherein the reservoir is configured to house the first therapeutic fluid and the pump is housed within the housing.

17. The implantable therapeutic fluid delivery system of claim 16, wherein the valve comprises a first valve connected to the first fluid pathway and a second valve connected to the second fluid pathway, and wherein the processor is configured to control actuation of the first valve to selectively open and close the first fluid pathway and to control actuation of the second valve to selectively open and close the second fluid pathway.

18. The implantable therapeutic fluid delivery system of claim 16, further comprising a third fluid pathway between the reservoir and the pump, and a second valve connected to the third fluid pathway, wherein the second valve is configured to control fluid communication between the reservoir and the pump.

19. The implantable therapeutic fluid delivery system of claim 18, further comprising a third valve interposed between the pump and the catheter connection port, wherein the processor is configured to control actuation of the second valve and the third valve when delivering therapeutic fluid from the reservoir to the catheter connection port.

20. The implantable therapeutic fluid delivery system of claim 1, wherein the reservoir comprises a first reservoir configured to house the first therapeutic fluid, the system further comprising a second reservoir configured to house a third therapeutic fluid, wherein the first fluid pathway extends from the valve to the first reservoir, and the system further comprises a third fluid pathway that extends from the valve to the second reservoir.

21. The implantable therapeutic fluid delivery system of claim 20, wherein the first reservoir and the second reservoir are disposed side-by-side within the housing.

22. The implantable therapeutic fluid delivery system of claim 20, wherein the first reservoir and the second reservoir are stacked within the housing.

23. The implantable therapeutic fluid delivery system of claim 20, wherein the valve comprises a first valve connected to the first fluid pathway, a second valve connected to the second fluid pathway, and a third valve connected to the third fluid pathway, wherein the processor is configured to control actuation of the first valve to open and close the first fluid pathway, to control actuation of the second valve to open and close the second fluid pathway, and to control actuation of the third valve to open and close the third fluid pathway.

24. The implantable therapeutic fluid delivery system of claim 23, wherein the first valve is configured to control fluid communication between the first reservoir and the pump, and the third valve is configured to control fluid communication between the second reservoir and the pump.

25. The implantable therapeutic fluid delivery system of claim 24, further comprising a fourth valve, wherein the fourth valve is interposed between the pump and the catheter connection port, and the processor is configured to control actuation of the fourth valve and at least one of the first valve or third valve when delivering therapeutic fluid from at least one of the first reservoir or the second reservoir to the catheter connection port.

26. The implantable therapeutic fluid delivery system of claim 1, further comprising:

a sensor configured to detect a fluid characteristic, wherein the valve is interposed between the first fluid pathway and the sensor and the second fluid pathway and the sensor.

27. The implantable therapeutic fluid delivery system of claim 1, further comprising:
one or more additional fluid pathways configured to convey one or more additional therapeutic fluids,
wherein the valve is connected to the one or more additional fluid pathways and wherein the processor is configured to actuate the valve to open and close each of the one or more additional fluid pathways.

28. The implantable therapeutic fluid delivery system of claim 27, wherein the valve comprises a plurality of valves connected to the first fluid pathway, the second fluid pathway, and the one or more additional fluid pathways, and wherein the processor is configured to control actuation of each of the plurality of valves to open and close the first fluid pathway, the second fluid pathway, and each of the one or more additional fluid pathways, respectively.

29. The implantable therapeutic fluid delivery system of claim 1, wherein the processor is housed within the housing.

30. The implantable therapeutic fluid delivery system of claim 1, wherein the valve comprises a single valve connected to both the first fluid pathway and the second fluid pathway, wherein the processor is configured to control actuation of the single valve to open the first fluid pathway while closing the second fluid pathway and wherein the processor is configured to control actuation of the single valve to close the first fluid pathway while opening the second fluid pathway.

31. A method comprising:
actuating, by a processor, a valve within an implantable therapeutic fluid delivery device to selectively open and close a first fluid pathway of the implantable fluid delivery device to control access to a reservoir fluidly connected to the first fluid pathway, and to selectively open and close a second fluid pathway of the implantable fluid delivery device to selectively access a catheter connection port configured to connect to a catheter, wherein the first fluid pathway is configured to convey a first therapeutic fluid, the second fluid pathway is configured to convey a second therapeutic fluid, the second fluid pathway is separate from the first fluid pathway, and the valve is connected to the first fluid pathway and the second fluid pathway,
wherein the implantable fluid delivery device comprises an inlet port configured to receive the first therapeutic fluid and the second therapeutic fluid, the valve being interposed between the inlet port and the reservoir along the first fluid flow pathway,
wherein the first fluid pathway extends from the inlet port to the catheter connection port and is fluidly connected to the catheter connection port, and the reservoir is interposed between the valve and the catheter connection port along the first fluid pathway,
wherein the first fluid pathway is fluidly connected to a pump, and the pump is interposed between the reservoir and the catheter connection port,
wherein the second fluid pathway extends from the inlet port to the catheter connection port and is directly fluidly connected to the catheter connection port without passing through any reservoir or any pump, and the valve is interposed between the inlet port and the catheter connection port along the second fluid pathway, and
controlling, by the processor, delivery of:

the first therapeutic fluid, via the first fluid pathway, from the inlet port, through the valve, through the reservoir, through the pump, and out the catheter connection port; and the second therapeutic fluid, via the second fluid pathway, from the inlet port, through the valve, and out the catheter connection port.

32. The method of claim 31, wherein the valve comprises a first valve connected to the first fluid pathway and a second valve connected to the second fluid pathway, and wherein actuating the valve comprises actuating the first valve to selectively open and close the first fluid pathway and actuating the second valve to selectively open and close the second fluid pathway.

33. The method of claim 31, further comprising:
sensing, by a sensor of the implantable therapeutic delivery device, entry of a needle into an aperture defined by the inlet port; and
storing, by the processor and in a memory, an indication when entry of the needle into the aperture defined by the inlet port is sensed.

34. The method of claim 31, further comprising receiving, by the processor, a user input, wherein actuating the valve comprises actuating the valve based at least upon the received user input.

35. The method of claim 31, further comprising displaying, by the processor, a fluid pathway indication when at least one of the first fluid pathway or the second fluid pathway is open.

36. The method of claim 34, further comprising sensing, by a sensor of the implantable therapeutic fluid delivery device, entry of a needle into an aperture defined by the inlet port, wherein actuating the valve comprises actuating the valve based at least upon a sensed entry of the needle into the aperture defined by the inlet port.

37. The method of claim 36, wherein actuating the valve comprises actuating the valve to be closed if entry of the needle into the aperture defined by the inlet port is sensed and the received user input did not indicate that the needle would be entering the aperture defined by the inlet port.

38. The method of claim 37, further comprising at least one of displaying an indication that entry of the needle into the aperture was sensed, issuing an audible, visual, or tactile alarm in response to sensing entry of the needle into the aperture defined by the inlet port and receiving user input that does not indicate that the needle would be entering the aperture defined by the inlet port, or storing an indication that entry of the needle into the aperture was sensed in a memory.

39. The method of claim 31, further comprising actuating, by the processor, a second valve connected to a third fluid pathway between the reservoir and the pump, wherein the second valve is configured to control fluid communication between the reservoir and the pump.

40. The method of claim 39, further comprising actuating, by the processor, the second valve and a third valve of the implantable therapeutic fluid delivery device interposed between the pump and the catheter connection port to deliver therapeutic fluid from the reservoir to the catheter connection port.

41. The method of claim 31, wherein the reservoir comprises a first reservoir, wherein the first fluid pathway extends from the valve to the first reservoir configured to house the first therapeutic fluid, and a third fluid pathway extends from the valve to a second reservoir configured to house a third therapeutic fluid.

42. The method of claim 41, wherein the valve comprises a first valve connected to the first fluid pathway, a second valve connected to the second fluid pathway, and a third valve connected to the third fluid pathway and wherein actuating the valve comprises actuating the first valve to open and close the first fluid pathway, actuating the second valve to open and close the second fluid pathway, and actuating the third valve to open and close the third fluid pathway.

43. The method of claim 42, wherein the first valve is configured to control fluid communication between the first reservoir and the pump of the therapeutic fluid delivery system, and the third valve is configured to control fluid communication between the second reservoir and the pump.

44. The method of claim 43, further comprising actuating a fourth valve interposed between the pump and the catheter connection port and between at least one of the first valve or the third valve to deliver therapeutic fluid from at least one of the first reservoir or the second reservoir to the catheter connection port.

45. A fluid delivery system comprising:
means for conveying a first therapeutic fluid;
means for conveying a second therapeutic fluid, the means for conveying the second therapeutic fluid being separate from the means for conveying the first therapeutic fluid;
a valve connected to the means for conveying the first therapeutic fluid and the means for conveying the second therapeutic fluid;
a pump, the first fluid pathway being fluidly connected to the pump;
means for storing the first therapeutic fluid, wherein the means for conveying the first therapeutic fluid is fluidly connected to the means for storing;
means for receiving the first therapeutic fluid and the second therapeutic fluid, wherein the valve is interposed between the means for receiving and the means for storing along the means for conveying the first therapeutic fluid;
a housing configured to be implanted in a patient, wherein the means for conveying the first therapeutic fluid, the means for conveying the second therapeutic fluid, the valve, and the means for storing are housed within the housing;
means for connecting a catheter to the housing,
wherein the means for conveying the first therapeutic fluid extends from the means for receiving the first therapeutic fluid and the second therapeutic fluid to the means for connecting the catheter to the housing, and wherein the means for conveying the first therapeutic fluid is connected to the means for connecting the catheter to the housing, and the means for storing is interposed between the valve and the means for connecting the catheter to the housing along the means for conveying the first therapeutic fluid, and
wherein the means for conveying the second therapeutic fluid extends from the means for receiving the first therapeutic fluid and the second therapeutic fluid to the means for connecting the catheter to the housing, and wherein the means for conveying the second therapeutic fluid is directly connected to the means for connecting the catheter to the housing without passing through any means for storing the first therapeutic fluid or any pump, and the valve is interposed between the means for receiving and the means for connecting to the catheter along the means for conveying the second therapeutic fluid; and means for actuating the valve to selectively open and close the means for conveying the first therapeutic fluid to control access to the means for storing, and to selectively open and close the means for conveying the second therapeutic fluid;

wherein the fluid delivery system is configured to deliver:

the first therapeutic fluid, via the means for conveying the first therapeutic fluid, from the means for receiving, through the valve, through the means for storing, through the pump, and out the means for connecting the catheter to the housing; and the second therapeutic fluid, via the means for conveying the second therapeutic fluid, from the means for receiving, through the valve, and out the means for connecting the catheter.

* * * * *